United States Patent
Estes et al.

(10) Patent No.: US 10,632,257 B2
(45) Date of Patent: Apr. 28, 2020

(54) ACTIVITY SENSING TECHNIQUES FOR AN INFUSION PUMP SYSTEM

(71) Applicant: Bigfoot Biomedical, Inc., Milpitas, CA (US)

(72) Inventors: Mark C. Estes, Malibu, CA (US); Deb Ruppert, Ramsey, NJ (US)

(73) Assignee: Bigfoot Biomedical, Inc., Milpitas, CA (US)

(*) Notice: Subject to any disclaimer, the term of this patent is extended or adjusted under 35 U.S.C. 154(b) by 0 days.

(21) Appl. No.: 16/178,689

(22) Filed: Nov. 2, 2018

(65) Prior Publication Data

US 2019/0070361 A1  Mar. 7, 2019

Related U.S. Application Data

(60) Continuation of application No. 15/285,872, filed on Oct. 5, 2016, now Pat. No. 10,117,993, which is a
(Continued)

(51) Int. Cl.
*A61M 5/172* (2006.01)
*A61M 5/14* (2006.01)
(Continued)

(52) U.S. Cl.
CPC ........ *A61M 5/1723* (2013.01); *A61M 5/1413* (2013.01); *A61M 5/14244* (2013.01);
(Continued)

(58) Field of Classification Search
CPC ......... A61M 2005/14208; A61M 2005/14268; A61M 2005/31518; A61M 2202/04;
(Continued)

(56) References Cited

U.S. PATENT DOCUMENTS

| | | |
|---|---|---|
| 2,605,765 A | 8/1952 | Kollsman |
| 3,886,938 A | 6/1975 | Szabo et al. |

(Continued)

FOREIGN PATENT DOCUMENTS

| | | |
|---|---|---|
| CA | 2543545 | 5/2005 |
| DE | 196 27 619 | 1/1998 |

(Continued)

OTHER PUBLICATIONS

International Search Report & Written Opinion, PCT/US2008/069960, dated Oct. 23, 2008, 19 pages.
(Continued)

*Primary Examiner* — Imani N Hayman
(74) *Attorney, Agent, or Firm* — Fish & Richardson P.C.

(57) ABSTRACT

Some embodiments of a wearable infusion pump system can include a pump device having a drive system to dispense a medicine to a user, an activity sensor that detects a possible change in an activity level of the user, and a controller to activate the drive system to dispense the medicine to the user. The controller device can query the user to indicate whether a detected activity level of the user represents an actual change in the activity level of the user. The controller device can alter the medicine dispensing schedule based on the user indicated changes in activity level.

22 Claims, 19 Drawing Sheets

Related U.S. Application Data continuation of application No. 14/987,004, filed on Jan. 4, 2016, now abandoned, which is a continuation of application No. 14/548,953, filed on Nov. 20, 2014, now Pat. No. 9,254,362, which is a continuation of application No. 14/098,742, filed on Dec. 6, 2013, now Pat. No. 8,894,628, which is a continuation of application No. 13/616,164, filed on Sep. 14, 2012, now Pat. No. 8,622,990, which is a continuation of application No. 13/025,857, filed on Feb. 11, 2011, now Pat. No. 8,328,754, which is a division of application No. 11/852,110, filed on Sep. 7, 2007, now Pat. No. 7,935,076.

(51) Int. Cl.
*A61M 5/142* (2006.01)
*G06F 19/00* (2018.01)
*G16H 20/17* (2018.01)
*A61M 5/145* (2006.01)
*A61M 5/315* (2006.01)

(52) U.S. Cl.
CPC ............ *A61M 5/172* (2013.01); *G06F 19/00* (2013.01); *G06F 19/3468* (2013.01); *G16H 20/17* (2018.01); *A61M 5/14566* (2013.01); *A61M 2005/14208* (2013.01); *A61M 2005/14268* (2013.01); *A61M 2005/31518* (2013.01); *A61M 2202/04* (2013.01); *A61M 2205/18* (2013.01); *A61M 2205/3569* (2013.01); *A61M 2205/502* (2013.01); *A61M 2230/005* (2013.01); *A61M 2230/201* (2013.01); *A61M 2230/63* (2013.01)

(58) Field of Classification Search
CPC ...... A61M 2205/18; A61M 2205/3569; A61M 2205/502; A61M 2230/005; A61M 2230/201; A61M 2230/63; A61M 5/1413; A61M 5/14244; A61M 5/14566; A61M 5/172; A61M 5/1723; G06F 19/00; G06F 19/3468; G16H 20/17
See application file for complete search history.

(56) References Cited

U.S. PATENT DOCUMENTS

| | | |
|---|---|---|
| 4,077,405 A | 3/1978 | Haerten et al. |
| 4,231,368 A | 11/1980 | Becker |
| 4,265,241 A | 5/1981 | Portner et al. |
| 4,300,554 A | 11/1981 | Hessberg et al. |
| 4,313,439 A | 2/1982 | Babb et al. |
| 4,398,908 A | 8/1983 | Siposs |
| 4,435,173 A | 3/1984 | Siposs et al. |
| 4,443,218 A | 4/1984 | DeCant, Jr. et al. |
| 4,493,704 A | 1/1985 | Beard et al. |
| 4,529,401 A | 7/1985 | Leslie et al. |
| 4,850,817 A | 7/1989 | Nason et al. |
| 5,045,064 A | 9/1991 | Idriss |
| 5,088,981 A | 2/1992 | Howson et al. |
| 5,190,522 A | 3/1993 | Wojcicki et al. |
| 5,250,027 A | 10/1993 | Lewis et al. |
| 5,261,882 A | 11/1993 | Sealfon et al. |
| 5,314,412 A | 5/1994 | Rex |
| 5,335,994 A | 8/1994 | Weynant Nee Girones |
| 5,338,157 A | 8/1994 | Blomquist |
| 5,342,180 A | 8/1994 | Daoud |
| 5,395,340 A | 3/1995 | Lee |
| 5,411,487 A | 5/1995 | Castagna |
| 5,545,143 A | 8/1996 | Fischell et al. |
| 5,551,850 A | 9/1996 | Williamson et al. |
| 5,569,186 A | 10/1996 | Lord et al. |
| 5,626,566 A | 5/1997 | Petersen et al. |
| 5,637,095 A | 6/1997 | Nason et al. |
| 5,665,065 A | 9/1997 | Colman et al. |
| 5,741,216 A | 4/1998 | Hemmingsen et al. |
| 5,772,635 A | 6/1998 | Dastur et al. |
| 5,816,306 A | 10/1998 | Giacomel |
| 5,852,803 A | 12/1998 | Ashby, III et al. |
| 5,919,167 A | 7/1999 | Mulhauser |
| 5,925,018 A | 7/1999 | Ungerstedt |
| 5,928,201 A | 7/1999 | Poulsen et al. |
| 5,947,934 A | 9/1999 | Hansen et al. |
| 5,951,530 A | 9/1999 | Steengaard et al. |
| 5,957,889 A | 9/1999 | Poulsen et al. |
| 5,984,894 A | 11/1999 | Poulsen et al. |
| 5,984,897 A | 11/1999 | Petersen et al. |
| 5,997,475 A | 12/1999 | Bortz |
| 6,003,736 A | 12/1999 | Ljunggren |
| 6,010,485 A | 1/2000 | Buch-Rasmussen et al. |
| 6,033,377 A | 3/2000 | Rasmussen et al. |
| 6,045,537 A | 4/2000 | Klitmose |
| 6,074,372 A | 6/2000 | Hansen |
| 6,110,149 A | 8/2000 | Klitgaard et al. |
| 6,126,595 A | 10/2000 | Amano |
| 6,156,014 A | 12/2000 | Petersen et al. |
| 6,171,276 B1 | 1/2001 | Lippe et al. |
| 6,231,540 B1 | 5/2001 | Smedegaard |
| 6,233,471 B1 | 5/2001 | Berner et al. |
| 6,248,067 B1 | 6/2001 | Causey, III et al. |
| 6,248,090 B1 | 6/2001 | Jensen et al. |
| 6,248,093 B1 | 6/2001 | Moberg |
| 6,277,098 B1 | 8/2001 | Klitmose et al. |
| 6,302,855 B1 | 10/2001 | Lav et al. |
| 6,302,869 B1 | 10/2001 | Klitgaard |
| 6,375,638 B2 | 4/2002 | Nason et al. |
| 6,379,339 B1 | 4/2002 | Klitgaard et al. |
| 6,381,496 B1 | 4/2002 | Meadows et al. |
| 6,397,098 B1 | 5/2002 | Uber, III et al. |
| 6,404,098 B1 | 6/2002 | Kayama et al. |
| 6,427,088 B1 | 7/2002 | Bowman, IV et al. |
| 6,461,331 B1 | 10/2002 | Van Antwerp |
| 6,474,219 B2 | 11/2002 | Klitmose et al. |
| 6,485,461 B1 | 11/2002 | Mason et al. |
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |
| 6,540,672 B1 | 4/2003 | Simonsen et al. |
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,572,542 B1 | 6/2003 | Houben |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,605,067 B1 | 8/2003 | Larsen |
| 6,613,019 B2 | 9/2003 | Munk |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B2 | 12/2003 | Kasuga et al. |
| 6,659,980 B2 | 12/2003 | Moberg et al. |
| 6,663,602 B2 | 12/2003 | Moller |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,691,043 B2 | 2/2004 | Ribeiro, Jr. |
| 6,692,457 B2 | 2/2004 | Flaherty |

(56) References Cited

U.S. PATENT DOCUMENTS

| | | |
|---|---|---|
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,723,077 B2 | 4/2004 | Pickup et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman, IV et al. |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larson et al. |
| 7,014,625 B2 | 3/2006 | Bengtsson |
| 7,018,360 B2 | 3/2006 | Flaherty et al. |
| 7,025,743 B2 | 4/2006 | Mann |
| 7,029,455 B2 | 4/2006 | Flaherty |
| 7,054,836 B2 | 5/2006 | Christensen et al. |
| 7,104,972 B2 | 9/2006 | Moller et al. |
| 7,128,727 B2 | 10/2006 | Flaherty et al. |
| 7,133,329 B2 | 11/2006 | Skyggebjerg et al. |
| 7,232,423 B2 | 6/2007 | Mernoe et al. |
| 2001/0056262 A1 | 12/2001 | Cabiri |
| 2002/0004651 A1 | 1/2002 | Ljndggreen et al. |
| 2002/0007154 A1 | 1/2002 | Hansen et al. |
| 2002/0040208 A1 | 4/2002 | Flaherty et al. |
| 2002/0091358 A1 | 7/2002 | Klitmose |
| 2002/0126036 A1 | 9/2002 | Flaherty et al. |
| 2003/0055380 A1 | 3/2003 | Flaherty |
| 2003/0065308 A1 | 4/2003 | Lebel et al. |
| 2003/0088238 A1 | 5/2003 | Poulsen |
| 2003/0104982 A1 | 6/2003 | Wittmann et al. |
| 2003/0199825 A1 | 10/2003 | Flaherty |
| 2003/0216683 A1 | 11/2003 | Shekalim |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0171983 A1 | 9/2004 | Sparks et al. |
| 2004/0176727 A1 | 9/2004 | Shekalim |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0065760 A1 | 3/2005 | Murtfeldt et al. |
| 2005/0090808 A1 | 4/2005 | Malave et al. |
| 2005/0095063 A1 | 5/2005 | Fathallah |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0238507 A1 | 10/2005 | DiIanni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2006/0041229 A1 | 2/2006 | Garibotto et al. |
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0178633 A1 | 8/2006 | Garibotto et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0247581 A1 | 11/2006 | Pedersen et al. |
| 2007/0073228 A1 | 3/2007 | Mernoe et al. |
| 2007/0073235 A1 | 3/2007 | Estes et al. |
| 2007/0073236 A1 | 3/2007 | Mernoe et al. |
| 2007/0124002 A1 | 5/2007 | Estes et al. |
| 2007/0156092 A1 | 7/2007 | Estes et al. |
| 2007/0167905 A1 | 7/2007 | Estes et al. |
| 2007/0167912 A1 | 7/2007 | Causey et al. |
| 2008/0125700 A1 | 5/2008 | Moberg et al. |
| 2008/0125701 A1* | 5/2008 | Moberg .......... A61B 5/1118 604/67 |
| 2008/0172027 A1 | 7/2008 | Blomquist |
| 2008/0306444 A1 | 12/2008 | Brister |

FOREIGN PATENT DOCUMENTS

| | | |
|---|---|---|
| DE | 102 36 669 | 2/2004 |
| DE | 20 2005 012 358 | 10/2005 |
| EP | 0 496 141 | 7/1992 |
| EP | 0 612 004 | 8/1994 |
| EP | 0 580 723 | 10/1995 |
| EP | 1 045 146 | 10/2000 |
| EP | 1 136 698 | 9/2001 |
| EP | 1 177 802 | 2/2002 |
| EP | 0 721 358 | 5/2002 |
| EP | 1 495 775 | 1/2005 |
| EP | 1 527 792 | 5/2005 |
| EP | 1 754 498 | 2/2007 |
| FR | 2 585 252 | 1/1987 |
| GB | 747 701 | 4/1956 |
| GB | 2 218 831 | 11/1989 |
| WO | WO 1990/15928 | 12/1990 |
| WO | WO 1997/21457 | 6/1997 |
| WO | WO 1998/11927 | 3/1998 |
| WO | WO 1998/57683 | 12/1998 |
| WO | WO 1999/21596 | 5/1999 |
| WO | WO 1999/39118 | 8/1999 |

(56) References Cited

FOREIGN PATENT DOCUMENTS

| WO | WO 1999/48546 | 9/1999 |
|---|---|---|
| WO | WO 2001/72360 | 10/2001 |
| WO | WO 2001/91822 | 12/2001 |
| WO | WO 2001/91833 | 12/2001 |
| WO | WO 2002/40083 | 5/2002 |
| WO | WO 2002/057627 | 7/2002 |
| WO | WO 2002/100469 | 12/2002 |
| WO | WO 2003/103763 | 12/2003 |
| WO | WO 2004/056412 | 7/2004 |
| WO | WO 2004/093648 | 11/2004 |
| WO | WO 2004/110526 | 12/2004 |
| WO | WO 2005/002652 | 1/2005 |
| WO | WO 2005/039673 | 5/2005 |
| WO | WO 2005/072794 | 8/2005 |
| WO | WO 2005/072795 | 8/2005 |
| WO | WO 2006/075016 | 7/2006 |
| WO | WO 2006/105792 | 10/2006 |
| WO | WO 2006/105793 | 10/2006 |
| WO | WO 2006/105794 | 10/2006 |

OTHER PUBLICATIONS

International Search Report & Written Opinion, PCT/US2008/069948, dated Jan. 23, 2009, 20 pages.

Invitation to Pay Fees, PCT/US2008/069948, dated Nov. 4, 2008, 13 pages.

Medtronic News Release, "Medtronic Receives FDA Approval for World's First Insulin Pump with Real-time Continuous Glucose Monitoring," Apr. 13, 2006, 3 pages.

*Debiotech News Release*, "Debiotech reveals its new miniaturized Disposable Insulin Nanopump™ for Diabetes therapy," available at http://www.debiotech.com/news/nw_159.html Apr. 24, 2006, 3 pages.

Patent Abstracts of Japan, vol. 1999, No. 04, and JP 11 010036, Apr. 30, 1999 and Jan. 19, 1999, Toray Ind. Inc.

International Preliminary Report on Patentability for Application PCT/US2008/069948, dated Mar. 18, 2010, 12 pages.

International Preliminary Report on Patentability for Application No. PCT/US2008/069960, dated Mar. 28, 2010, 9 pages.

\* cited by examiner

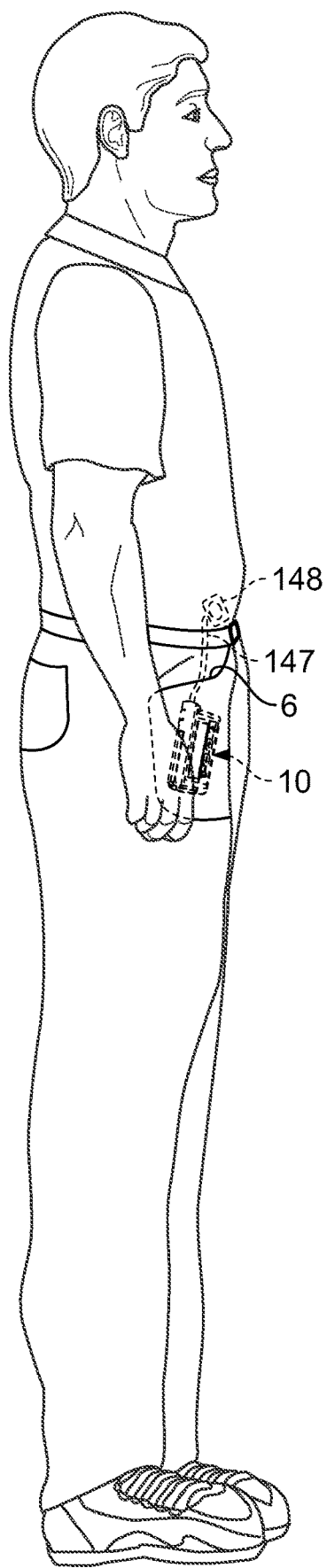
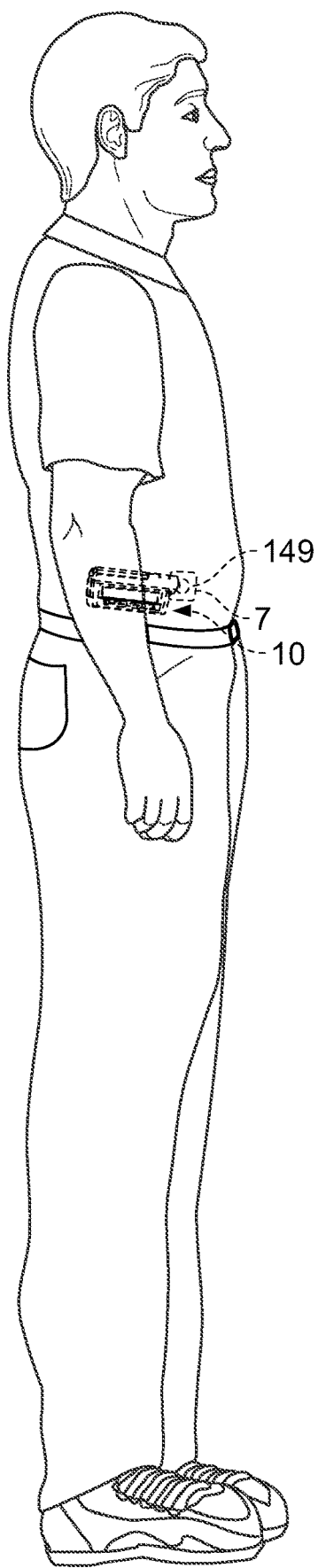
FIG. 7
FIG. 8

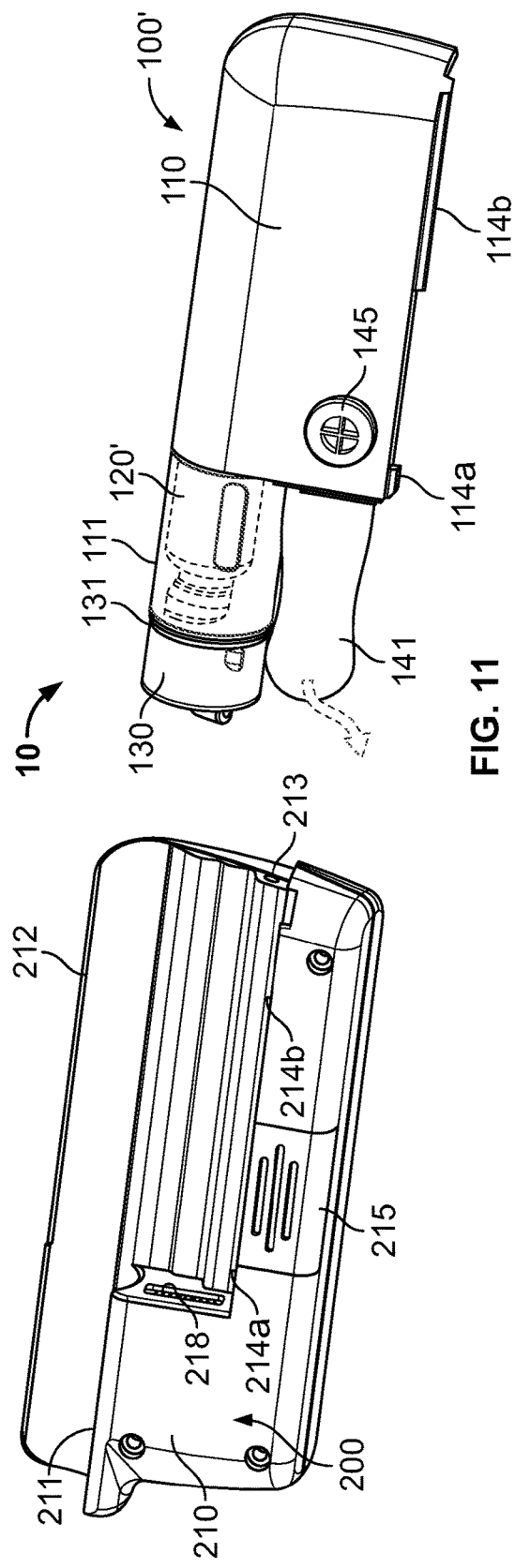
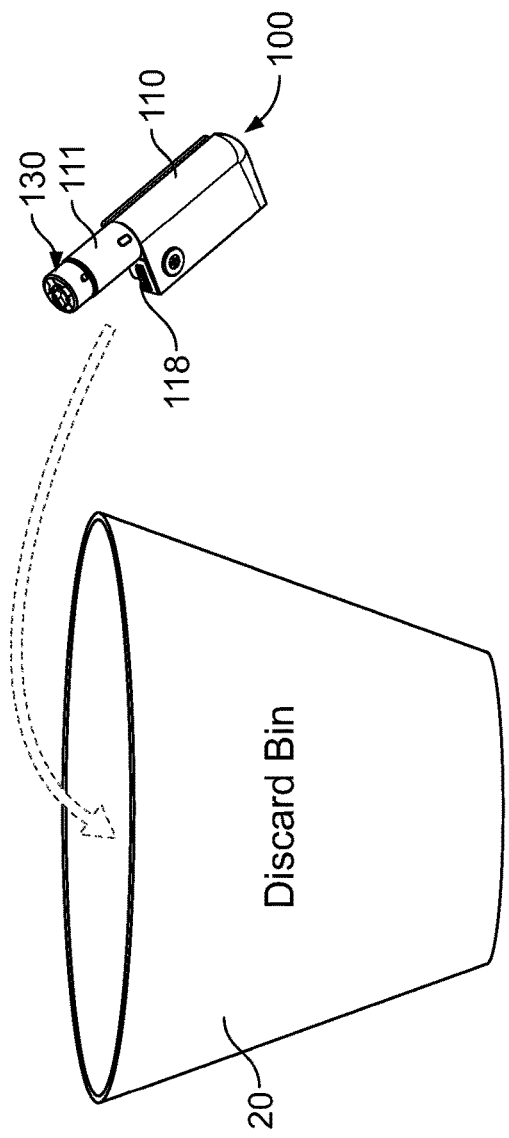
FIG. 11
FIG. 12

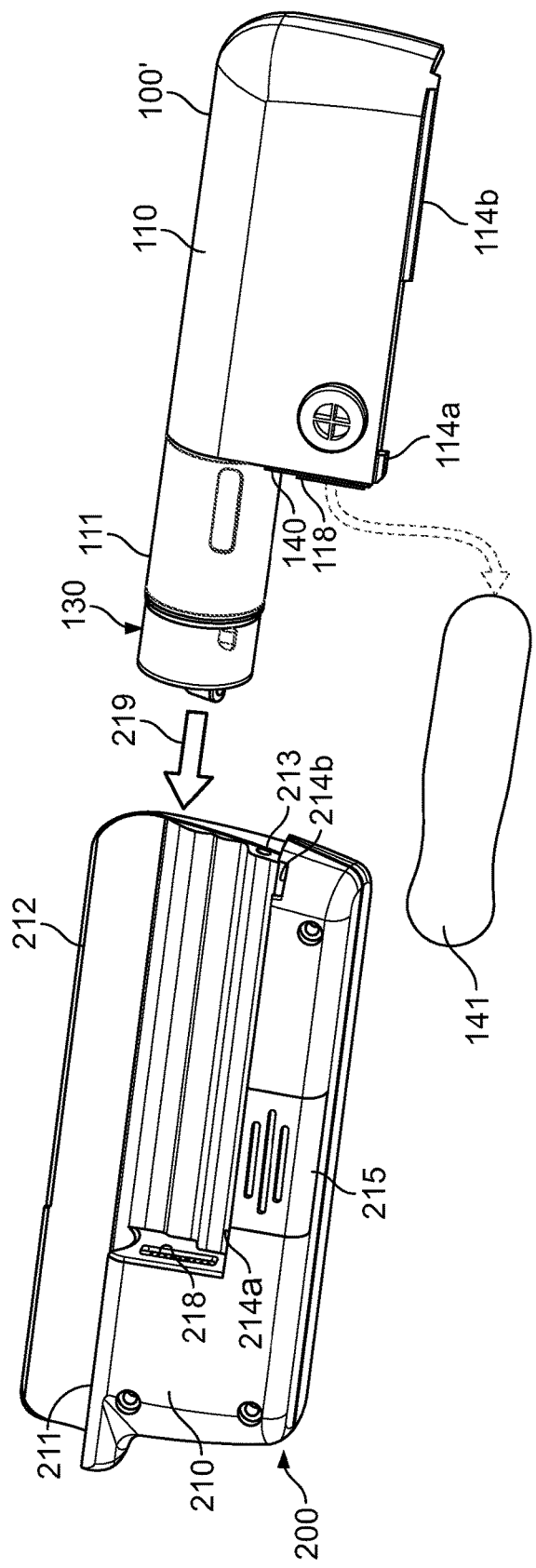
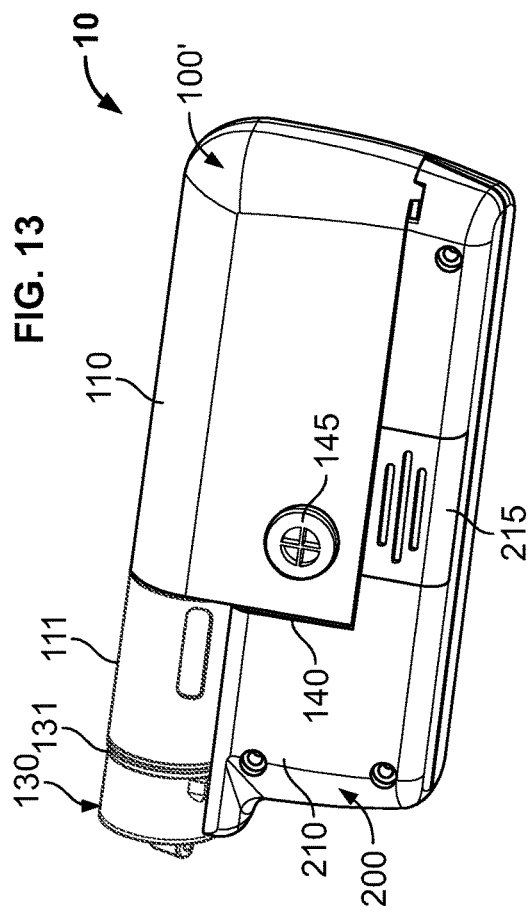
FIG. 13
FIG. 14

ACTIVITY SENSING TECHNIQUES FOR AN INFUSION PUMP SYSTEM

CROSS-REFERENCE TO RELATED APPLICATIONS(S)

This application is a continuation of U.S. application Ser. No. 15/285,872, which is a continuation of U.S. application Ser. No. 14/987,004 filed Jan. 4, 2016, which is a continuation of U.S. application Ser. No. 14/548,953 (now U.S. Pat. No. 9,254,362) filed Nov. 20, 2014, which is a continuation of U.S. application Ser. No. 14/098,742 (now U.S. Pat. No. 8,894,628) filed Dec. 6, 2013, which is a continuation of U.S. application Ser. No. 13/616,164 filed Sep. 14, 2012 (now U.S. Pat. No. 8,622,990), which is a continuation of U.S. application Ser. No. 13/025,857 filed Feb. 11, 2011 (now U.S. Pat. No. 8,328,754), which is a divisional of U.S. application Ser. No. 11/852,110 filed Sep. 7, 2007 (now U.S. Pat. No. 7,935,076), the entire disclosures of these prior related applications being incorporated herein by reference.

TECHNICAL FIELD

This document relates to sensing activity of a user of an infusion pump system.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels.

SUMMARY

Physical exercise can sometimes change an individual's need for medicine. For example, physical exercise can reduce an individual's need for insulin. Accordingly, some embodiments of a wearable infusion pump system may include an activity sensor that monitors a user's activity while the pump system is carried or otherwise worn by the user. In some circumstances, the activity sensor can detect the user's movement characteristics, the user's physiological parameters, or a combination thereof, which may be indicative of physical exercise or the like. In other circumstances, the activity sensor can monitor the user's movement to determine if the user is experiencing a seizure. Such activity sensing techniques may be employed so as to adjust a medicine dispensing regimen to the needs of the pump system user.

In particular embodiments, a wearable infusion pump system may include a pump device including a drive system to dispense a medicine to a user, an activity sensor, and a controller. The activity sensor can detect signals indicative of an activity level of the user. The controller can activate the drive system to dispense the medicine based on a medicine dispensing schedule. The controller can query the user to indicate whether a detected activity level of the user represents an actual activity level of the user and to alter the medicine dispensing schedule based on the user-indicated activity level.

In some embodiments, a method of administering medicinal fluid to a user can include delivering a medicinal fluid from a wearable pump system to the user, detecting an activity level of the user using an activity sensor in the pump system, querying the user on a user interface of the pump system to indicate whether the detected activity level of the user represents an actual activity level of the user, and adjusting the delivery of medicinal fluid from the pump system to the user in response to the user input that confirms the detected activity level represents the actual activity level of the user.

In particular embodiments, a method of administering medicinal fluid to a user experiencing a seizure may include delivering a medicinal fluid from a wearable pump system to the user, determining if the user is having a seizure, and adjusting the delivery of medicinal fluid from the pump system to the user in response to a detected seizure. Determining whether the user is having a seizure can include detecting an increased motion level of the user above a threshold motion level using an motion sensor in the pump system and detecting whether the user is lying horizontally.

In certain embodiments, a method of administering medicinal fluid to a user may include delivering a medicinal fluid from a wearable pump system to the user, detecting an activity level of the user using an activity sensor in the pump system, storing data correlating activity levels of the user to changes in the need for medicinal fluid of the user, the data being stored in computer-readable memory of the pump system, and adjusting the delivery of medicinal fluid from the pump system to the user in response to an activity level of the user and the stored data correlating activity levels to changes in the need for medicinal fluid.

In particular embodiments, a wearable infusion pump system may include a disposable and non-reusable pump device having a drive system to dispense insulin. The pump device can define a space to receive an insulin cartridge. The system can also include a reusable controller device removably attached to the pump device. The controller device can having control circuitry that communicates control signals to the drive system to dispense insulin at a dispensation rate when the controller device removably attached to the pump device. The controller device can include a user interface. The system can also include an activity sensor arranged in the reusable controller and electrically connected to the control circuitry. The activity sensor can provide signals indicative of activity levels of the user. The controller device can query the user to indicate whether a detected activity level of the user represents an actual change in the activity level of the user and alter the medicine dispensing schedule based on the user-indicated activity level.

Some or all of the embodiments described herein may provide one or more of the following advantages. First, some embodiments of an infusion pump system may include a configuration that detects and logs physical activity of the user. This configuration may permit the user of a wearable infusion pump to monitor physical activities and thereafter respond to such activities with selected dosing adjustments. Moreover, the recorded data of the user's physical activities can enhance the ability of the user or a medical practitioner to perform retrospective analysis and correction of the medicine delivery profile.

Second, some embodiments of the infusion pump system can operate to query the user when a particular level of physical activity or other movement characteristics are detected by the activity sensor. For example, the user interface of the infusion pump system can be employed to alert the user that a particular level of physical activity has been detected (e.g., due to the user exercising, participating in an athletic activity, or the like). In such circumstances, the user can be prompted to confirm the occurrence of the exercise or other physical activity. In response to the user's confirmation, the pump system can be configured to adjust the medicine dispensation rate or to suggest a modification to the medicine dispensation rate to the user.

Third, some embodiments of the infusion pump system may include a reusable controller device that is removably attachable to a disposable single-use pump device to provide an electrical connection therebetween. In these circumstances, the infusion pump system can include an activity sensor arranged in the reusable controller device such that the activity sensor is not discarded with the single-use pump device. Accordingly, the activity sensor instrumentation can be employed in a cost-effective manner that permits reuse of the instrumentation with a series of different pump devices.

Fourth, some embodiments of the pump device may be attached to the controller device so that a user can readily monitor infusion pump operation by simply viewing the user interface connected to the pump device. In these circumstances, the user may activate and control the pump device without the requirement of locating and operating a separate monitoring module.

Fifth, some embodiments of the infusion pump system may be configured to be portable, wearable, and (in some circumstances) concealable. For example, a user can conveniently wear the infusion pump system on the user's skin under clothing or can carry the pump device in the user's pocket (or other portable location) while receiving the medicine dispensed from the pump device.

The details of one or more embodiments are set forth in the accompanying drawings and the description below. Other features, objects, and advantages will be apparent from the description and drawings, and from the claims.

DESCRIPTION OF DRAWINGS

FIG. 7 is a perspective view of the infusion pump system of FIG. 6 worn on clothing of a user.

FIG. 8 is a perspective view of an infusion pump system worn on skin of a user, in accordance with particular embodiments.

FIGS. 11-12 are perspective views of the pump device of FIGS. 9-10 being discarded and the controller device of FIGS. 9-10 being reused with a new pump device.

FIGS. 13-14 are perspective views of the new pump device of FIG. 11 being attached to the controller device of FIG. 11.

DETAILED DESCRIPTION OF ILLUSTRATIVE EMBODIMENTS

Figure 1:
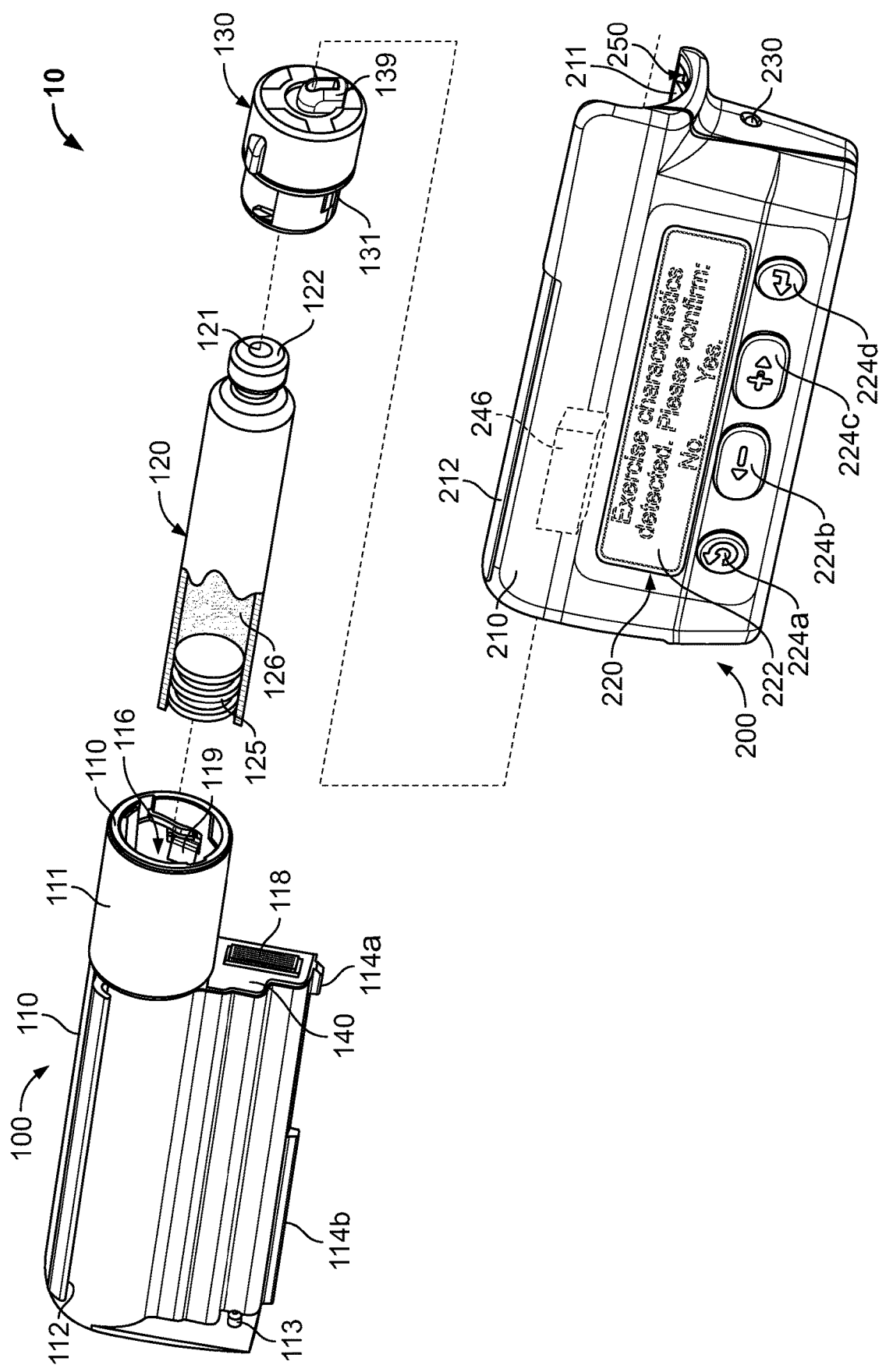
FIG. 1 is a perspective view of an infusion pump system in accordance with some embodiments.
Figure 2:
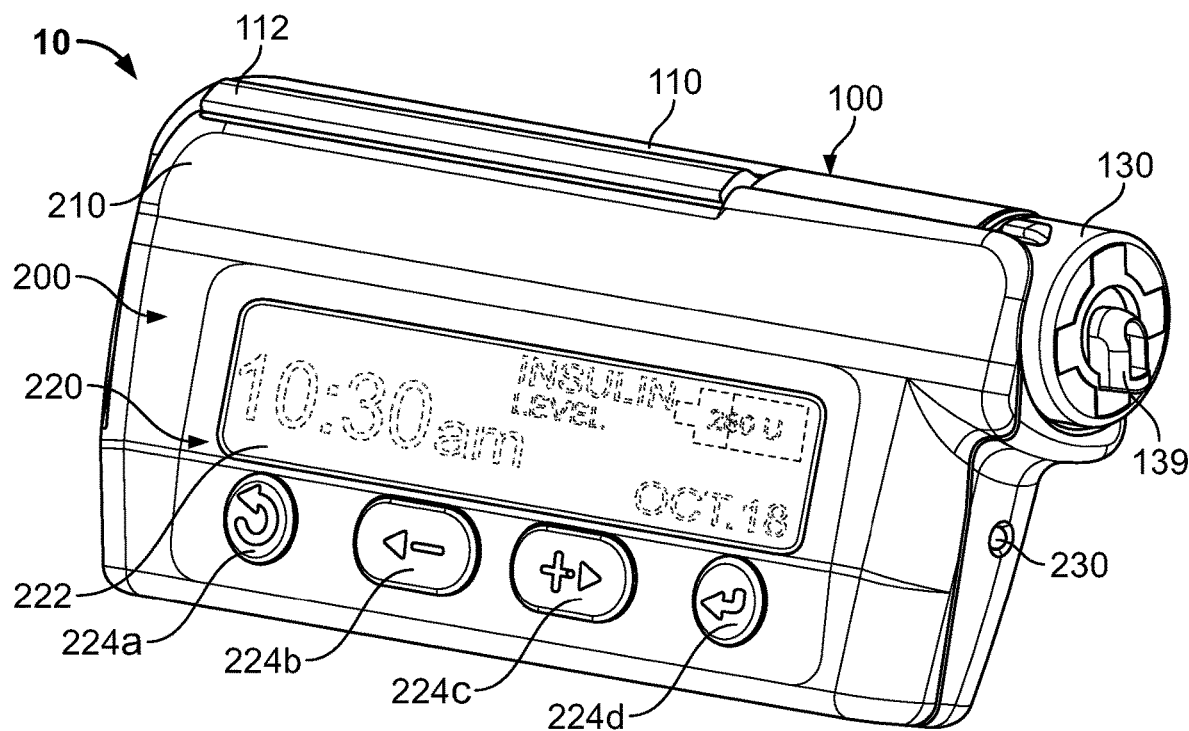
FIG. 2 is a perspective view of the infusion pump system of FIG. 1 in an assembled state.
Figure 3:
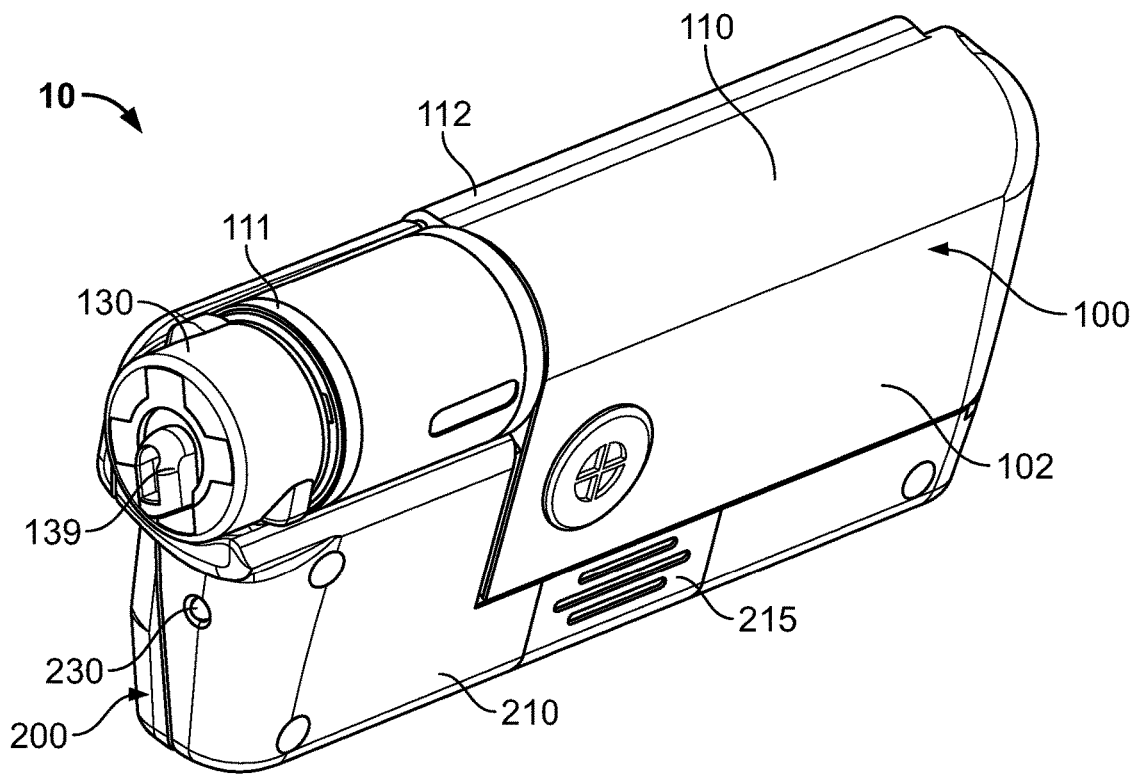
FIG. 3 is another perspective view of the infusion pump system of FIG. 2.

Referring to FIGS. 1-3, an infusion pump system 10 can include a pump device 100 and a controller device 200 that can communicate with the pump device 100. The pump device 100 can include a housing structure 110 that defines a cavity 116 in which a fluid cartridge 120 can be received. The pump device 100 also can include a cap device 130 to retain the fluid cartridge 120 in the cavity 116 of the housing structure 110. The pump device 100 can include a drive system (described in more detail below) that advances a plunger 125 in the fluid cartridge 120 so as to dispense fluid therefrom. The controller device 200 can communicate with the pump device 100 to control the operation of the drive system. When the controller device 200, the pump device 100 (including the cap device 130), and the fluid cartridge 120 are assembled together, the user can (in some embodiments) conveniently wear the infusion pump system 10 on the user's skin under clothing or in the user's pocket while receiving the fluid dispensed from the pump device 100.

The controller device 200 may be configured as a reusable component that provides electronics and a user interface to control the operation of the pump device 100. In such circumstances, the pump device 100 can be a disposable component that is disposed of after a single use. For example, as described in more detail below in connection with FIGS. 9-14, the pump device 100 can be a "one time use" component that is thrown away after the fluid cartridge 120 therein is exhausted. Thereafter, the user can removably attach a new pump device 100' (having a new medicine cartridge 120') to the reusable controller device 200 for the dispensation of fluid from a new fluid cartridge 120'. Accordingly, the user is permitted to reuse the controller device 200 (which may include complex or valuable electronics) while disposing of the relatively low-cost pump device 100 after each use. Such a pump system 10 can provide enhanced user safety as a new pump device 100 (and drive system therein) is employed with each new fluid cartridge 120.

The infusion pump system 10 may also include an activity sensor 246 that can detect movement activities of the user, physiological characteristics of the user, or a combination thereof. As discussed in further detail below in connection with FIG. 15, the activity sensor 246 may comprise, for example, a motion sensor (e.g., an accelerometer or the like), a pulse rate sensor, a blood pressure sensor, a body temperature sensor, a perspiration sensor, or the like. Furthermore, in some embodiments, the activity sensor 246 may include an inclination sensor to determine if the user is lying horizontally, rather than standing up or sitting up. As shown in FIG. 1, some embodiments of the activity sensor 246 that include a motion sensor can be housed in the controller device 200 and electrically connected to the control circuitry 240 (FIG. 15) therein. As such, the movement characteristics of the user can be detected and recorded while the pump system 10 (including the controller device 200) are carried or otherwise worn by the user.

Briefly, in use, the pump device 100 can be configured to be removably attach to the controller device 200 in a manner that provides a secure fitting, an overall compact size, and a reliable electrical connection that is resistant to water migration. For example, as described in more detail below in connection with FIGS. 1-5, the controller device 200 can include a housing 210 having a number of features that mate with complementary features of the pump housing 110. In such circumstances, the controller device 200 can be removably attached to the pump device 100 in a generally side-by-side configuration while not fully surrounding the pump housing 110. Accordingly, the pump device 100 and the controller device 200 can be separate components that fit together, but the overall size of the combined assembly can be reduced because there is no requirement for one component (e.g., the controller device) to completely surround or envelop the second component (e.g., the pump device). The compact size permits the infusion pump system 10 to be discrete and portable (as described below in connection with FIGS. 6-8). Moreover, at least one of the pump device 100 or the controller device 200 can include a release member that facilitates an easy-to-use detachment and replacement process.

Furthermore, in use, the controller device 200 or another portion of the pump system can include the activity sensor 246 that detects physical activity of the user. This configuration may permit the user of a wearable infusion pump system 10 to monitor physical activities and thereafter respond to such activities with selected dosing adjustments. For example, the user interface 220 of the infusion pump system can be employed to alert the user that a particular level of physical activity has been detected (e.g., due to the user exercising, participating in an athletic activity, or the like). In such circumstances, the user can be prompted to confirm the occurrence of the exercise or other physical activity (refer, for example, to the display device 222 in FIG. 1). In response to the user's confirmation, the pump system can be configured to adjust the medicine dispensation rate or to suggest a modification to the medicine dispensation rate to the user. Also, in certain embodiments, the recorded data of the user's physical activities can be used in a retrospective analysis (e.g., by the user or a medical practitioner) to make corrections to the medicine dispensing profile.

Referring again to FIGS. 1-3, the pump system 10 can be a medical infusion pump system that is configured to controllably dispense a medicine from the cartridge 120. As such, the fluid cartridge 120 can contain a medicine 126 (FIG. 1) to be infused into the tissue or vasculature of a targeted individual, such as a human or animal patient. For example, the pump device 100 can be adapted to receive a medicine cartridge 120 in the form of a carpule that is preloaded with insulin or another medicine for use in the treatment of Diabetes (e.g., Byetta®, Symlin®, or others). Such a cartridge 120 may be supplied, for example, by Eli Lilly and Co. of Indianapolis, Ind. Other examples of medicines contained in the fluid cartridge 120 include: pain relief drugs, hormone therapy, blood pressure treatments, anti-emetics, osteoporosis treatments, or other injectable medicines. The fluid cartridge 120 may have other configurations. For example, the fluid cartridge may comprise a reservoir that is integral with the pump housing structure 110 (e.g., the fluid cartridge can be defined by one or more walls of the pump housing structure 110 that surround a plunger to define a reservoir in which the medicine is injected or otherwise received).

In some embodiments, the pump device 100 can include one or more structures that interfere with the removal of the medicine cartridge 120 after the medicine cartridge 120 is inserted into the cavity 116. For example, as shown in FIG. 1, the pump housing structure 110 can include one or more retainer wings 119 that at least partially extend into the cavity 116 to engage a portion of the medicine cartridge 120 when the medicine cartridge 120 is installed therein. Such a configuration may facilitate the "one-time-use" feature of the pump device 100. In some embodiments, the retainer wings 119 interfere with attempts to remove the medicine cartridge 120 from the pump device 100, thus ensuring that the pump device 100 will be discarded along with the medicine cartridge 120 after the medicine cartridge 120 is emptied, expired, or otherwise exhausted. Accordingly, the pump device 100 can operate in a tamper-resistant and safe manner because the pump device 100 can be designed with predetermined life expectancy (e.g., the "one-time-use" feature in which the pump device is discarded after the medicine cartridge 120 is emptied, expired, or otherwise exhausted).

Still referring to FIGS. 1-3, the controller device 200 can be removably attached to the pump device 100 so that the two components are mechanically mounted to one another in a fixed relationship. Such a mechanical mounting can form an electrical connection between the removable controller device 200 and the pump device 100. For example, the controller device 200 can be in electrical communication with a portion of a drive system (not shown in FIGS. 1-3) of the pump device 100. As described in more detail below, the pump device 100 can include a drive system that causes controlled dispensation of the medicine or other fluid from the cartridge 120. In some embodiments, the drive system incrementally advances a piston rod (not shown in FIGS. 1-3) longitudinally into the cartridge 120 so that the fluid is forced out of an output end 122. A septum 121 (FIG. 1) at the output end 122 of the fluid cartridge 120 can be pierced to permit fluid outflow when the cap device 130 is connected to the pump housing structure 110 (described in more detail below). Thus, when the pump device 100 and the controller device 200 are attached and thereby electrically connected, the controller device 200 can communicate electronic control signals via a hardwire-connection (e.g., electrical contacts or the like) to the drive system or other components of the pump device 100. In response to the electrical control signals from the controller device 200, the drive system of the pump device 100 causes medicine to incrementally dispense from the medicine cartridge 120.

As shown in FIG. 1, the pump device 100 can include an electrical connector 118 (e.g., having conductive pads, pins, and the like) that are exposed to the controller device 200 and that mate with a complementary electrical connector (refer to connector 218 in FIG. 4) on the adjacent face of the controller device 200. The electrical connectors 118 and 218 provide the electrical communication between the control circuitry (refer, for example, to FIG. 15) housed in the controller device 200 and at least a portion of the drive system or other components of the pump device 100. For example, in some embodiments, the electrical connectors 118 and 218 can permit the transmission of electrical control signals to the pump device 100 and the reception of feedback signals (e.g., sensor signals) from particular components within the pump device 100. Furthermore, as described in more detail below, the infusion pump system 10 can include a gasket 140 that provides a seal that is resistant to migration of external contaminants when the pump device 100 is attached to the controller device 200. Thus, in some embodiments, the infusion pump system 10 can be assembled into a water resistant configuration that protects the electrical interconnection from water migration (e.g., if the user encounters water while carrying the pump system 10).

Still referring to FIGS. 1-3, the controller device 200 can include a user interface 220 that permits a user to monitor the operation of the pump device 100. In some embodiments, the user interface 220 includes a display device 222 and one or more user-selectable buttons (e.g., four buttons 224a, 224b, 224c, and 224d in this embodiment). The display device 222 can include an active area in which numerals, text, symbols, images, or a combination thereof can be displayed (refer, for example, to FIG. 2). For example, the display device 222 can be used to communicate a number of settings or menu options for the infusion pump system 10. In this embodiment, the user may press one or more of the buttons 224a, 224b, 224c, and 224d to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). In some embodiments, the user can adjust the settings or otherwise program the controller device 200 by pressing one or more buttons 224a, 224b, 224c, and 224d of the user interface 220. For example, in embodiments of the infusion pump system 10 configured to dispense insulin, the user may press one or more of the buttons 224a, 224b, 224c, and 224d to change the dispensation rate of insulin or to request that a bolus of insulin be dispensed immediately or at a scheduled, later time. Also, the user can activate the illumination instrument 230 on the controller device 200 by pressing one or more buttons 224a, 224b, 224c, and 224d of the user interface 220.

Accordingly, when the controller device 200 is connected to the pump device 100, the user can be provided with the opportunity to readily monitor infusion pump operation by simply viewing the user interface 220 of the controller device 200 connected to the pump device 100. Such monitoring capabilities may provide comfort to a user who may have urgent questions about the current operation of the pump device 100. Also, in these embodiments, there may be no need for the user to carry and operate a separate module to monitor the operation of the infusion pump device 100, thereby simplifying the monitoring process and reducing the number of devices that must be carried by the user. If a need arises in which the user desires to monitor the operation of the pump device 100 or to adjust settings of the pump system 10 (e.g., to request a bolus amount of medicine), the user can readily operate the user interface 220 of the controller device 200, which is removably attached to the pump device 100, without the requirement of locating and operating a separate monitoring module.

Figure 4:
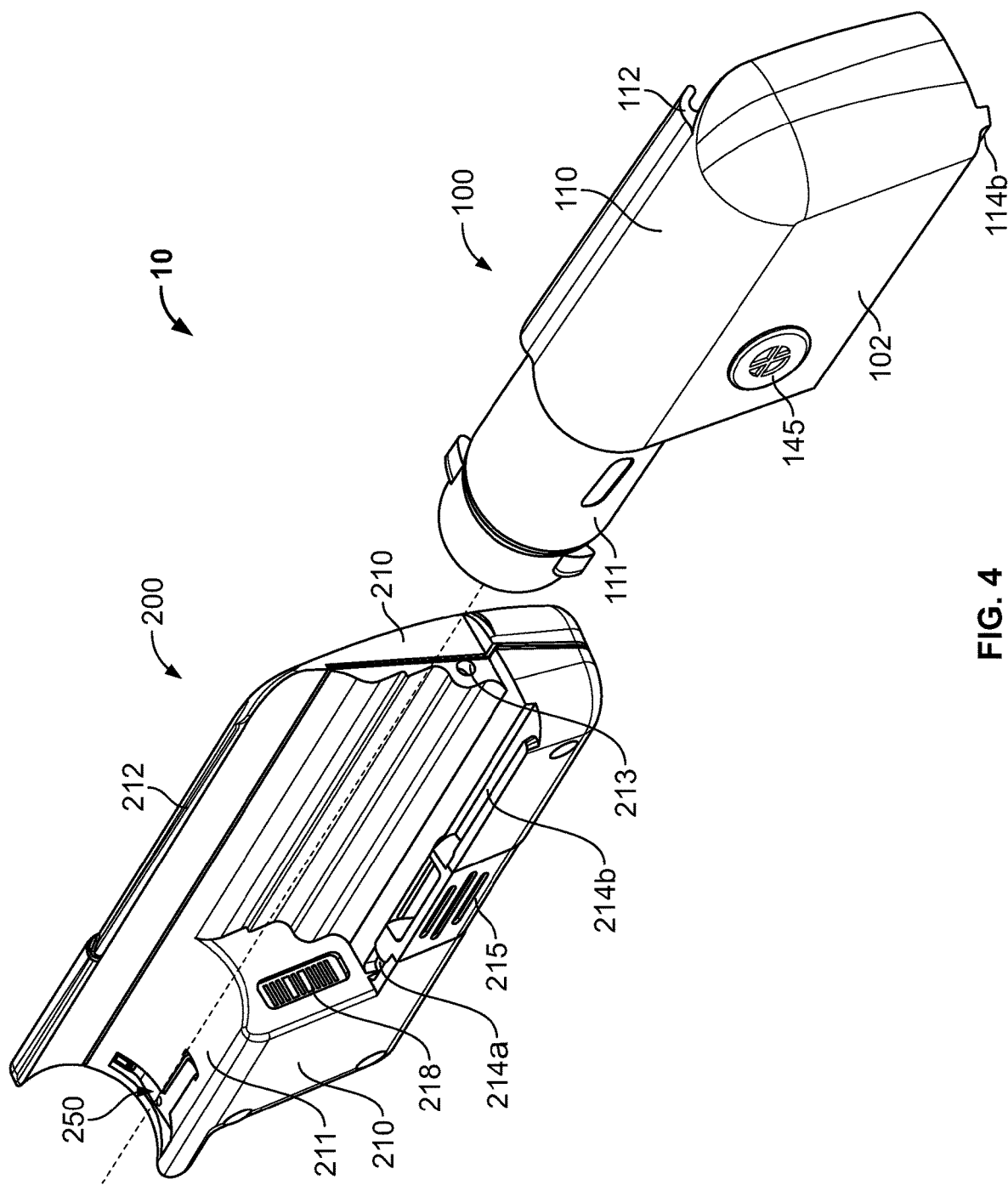
FIG. 4 is a perspective view of the infusion pump system of FIG. 1 in a detached state.
Figure 5:
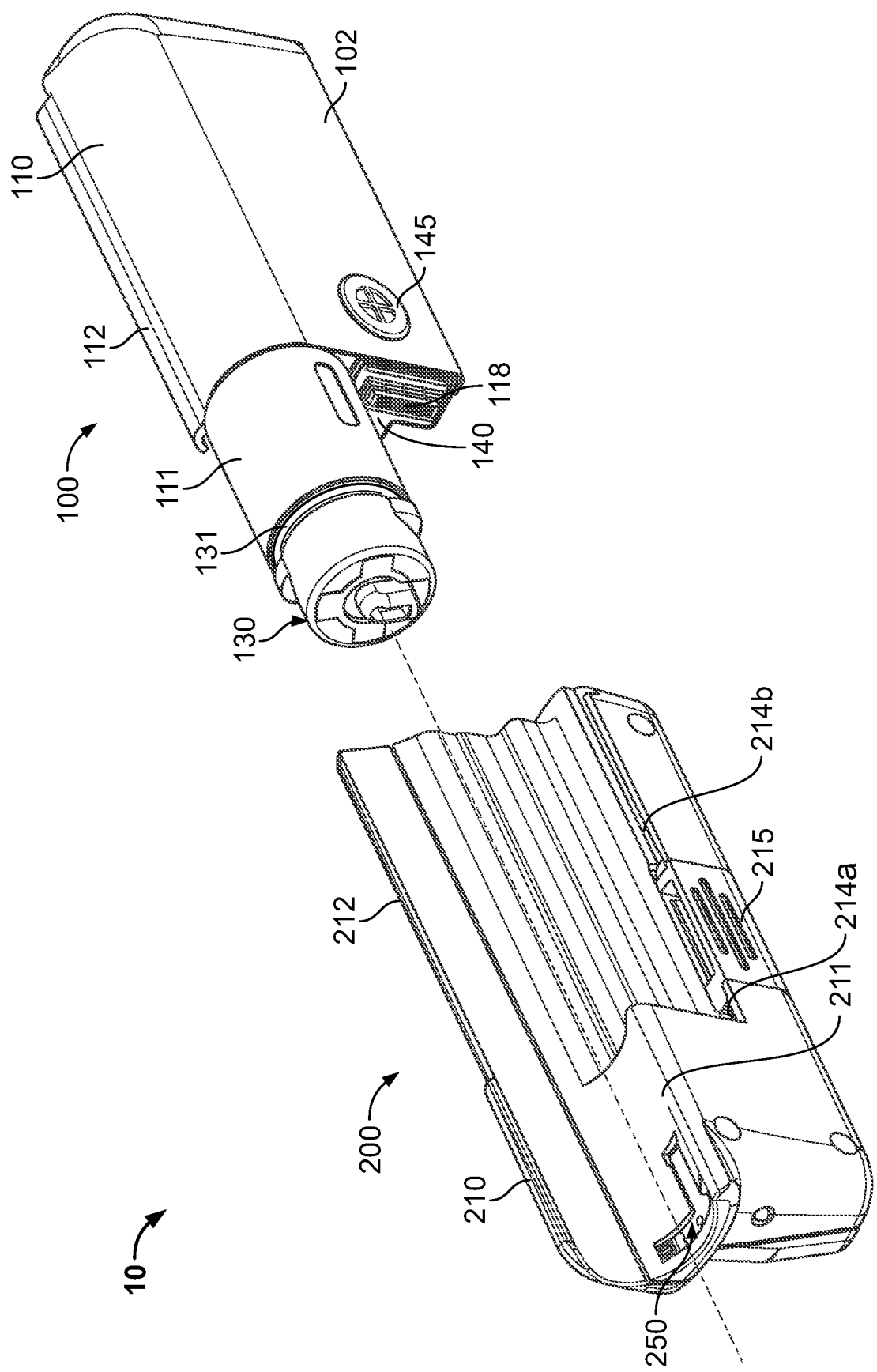
FIG. 5 is another perspective view of the infusion pump system on FIG. 4.

Referring now to FIGS. 4-5, when the infusion pump system 10 operates, the controller device 200 can be removably attached to the pump device 100 in a side-by-side arrangement. For example, the pump device 100 may be moved in a longitudinal direction (e.g., refer to direction 219 in FIG. 13) toward the controller device 200 until the complementary features connect and secure the separate components in the side-by-side arrangement. In these circumstances, the pump device 100 and the controller device 200 can be separate components that fit together, but the overall size of the combined assembly can be reduced because there is no requirement for one component (e.g., the controller device or pump device) to surround or envelop the second component (e.g., the pump device or controller device). Moreover, in some embodiments, the pump device 100 and controller device 200 can be readily attached together with a "one-movement" process that is convenient to the user.

The controller device 200 can include a controller housing structure 210 having a number of features that are configured to mate with complementary features of the pump housing structure 110 so as to form a releasable mechanical connection. For example, the pump housing structure 110 can include a barrel 111 that mates with a complementary barrel channel 211 of the controller housing 210. Also, the pump housing 110 can include slider channel 112 that slidably engages a complementary rail 212 defined by the controller housing 210. The slider channel 112 can guide the relative motion between the pump device 100 and the controller device 200 in the longitudinal direction during the attachment process. Similarly, the pump housing 110 can include a segmented rail 114a-b (FIG. 1) that mates with a guide channel 214a-b to direct the relative longitudinal motion between the pump device 100 and the controller device 200. As described in more detail below, the segmented rails 114a-b can interact with the release member 215 so as to releasably secure the pump device 100 into assembly with the controller device 200. In addition, the pump housing 110 can include an extension 113 (FIG. 1) that mates with a depression 213 (FIG. 5) in the controller housing 210 when the pump device 100 is fully attached to the controller device 200. It should be understood that, in other embodiments, other features or connector devices can be used to facilitate the side-by-side mounting arrangement. These other features or connector devices can include, for example, magnetic attachment device, mating tongues and grooves, mounting protrusions that friction fit into mating cavities, or the like.

Still referring to FIGS. 4-5, the pump device 100 and the controller device 200 can be attached in a manner that is resistant to migration of external contaminants (e.g., water, dirt, and the like) both into the pump housing structure 110 and the controller housing structure 210. For example, when the pump device 100 is advanced in the longitudinal direction toward the controller device 200 (as guided by the slider channel 112 and the segmented rails 114a-b), the electrical connector 118 (FIG. 5) of the pump device 100 is directed toward engagement with the mating connector 218 (FIG. 4) of the controller device 200. When the connectors 118 and 218 join together to form the electrical connection, the gasket 140 is compressed between the adjacent surfaces of the pump housing 110 and the controller housing 210. The gasket 140 thereby forms a water-resistant seal between the ambient environment and the mated connectors 118 and 218. Accordingly, in particular circumstances, the infusion pump system 10 can be assembled into a "water tight" configuration that protects sensitive internal components from water migration in the event that the user encounters water while wearing the pump system 10. In one example, the gasket 140 can resist migration of water to the electrical connectors 118 and 218 even when the system 10 is submerged underwater (e.g., in a pool, in a bath, or the like) for an extended period of time, such as at least 10 minutes, at least 30 minutes, at least one hour, at least two hours, and preferably at least four hours.

In addition, other paths for migration of external contaminants into the assembled pump system 10 can be sealed. For example, the infusion pump system 10 can include one or more seals that are arranged to hinder migration of external contaminants between the cap device 130 and the pump housing 110 into the cavity 116 of the pump device 100. In some embodiments, the seal 131 arranged between the cap device 130 and the barrel 111 can provide an effective water-resistant seal against water migration into the cavity. As such, the medicine cartridge 120 and pump drive system (not shown in FIGS. 4-5) can be protected during operation.

Still referring to FIGS. 4-5, some embodiments of the infusion pump system 10 may employ a power source arranged in pump device 100 or the controller device 200 that draws upon surrounding air for optimum operation. Because the controller device 200 and the pump device 100 may be sealed to resist water migration during normal usage, a water-resistant vent instrument 145 can be used to provide the air to the power source without permitting migration of water therethrough. For example, the pump device 100 can contain a first power source 345 in the form of a zinc-air cell battery (refer to FIG. 16), which draws upon the surrounding air during operation. When the pump device 100 is in use, the pump housing 110 can be sealed to protect the internal drive system and medicine cartridge from water migration. As such, the pump housing 110 can include a water-resistant vent instrument 145 disposed proximate to the first power source 345 (e.g., a zinc air cell battery) so that some air may pass through the vent 145 and toward the first power source 345. The water-resistant vent instrument 145 can include one or more layers of a material that is permeable to air and resistant to passage of liquids such as water. For example, the water-resistant vent instrument 145 can include one or more layers of a GORE-TEX material to resist the migration of water into the pump device while permitting the passage of air toward the battery.

Accordingly, the pump device 100 and the controller device 200 can be mounted to one another so that the assembled system 10 is resistant to water migration both into the pump housing structure 110 and the controller housing structure 210. Such a configuration can also provide water-resistant protection for the electrical connection between the pump device 100 and the controller 200. Thus, the sensitive internal components in the controller device 200 and the pump device 100 can be reliably protected from water migration if the user encounters water (e.g., rain, incidental splashing, and the like) while using the pump system 10.

Figure 6:
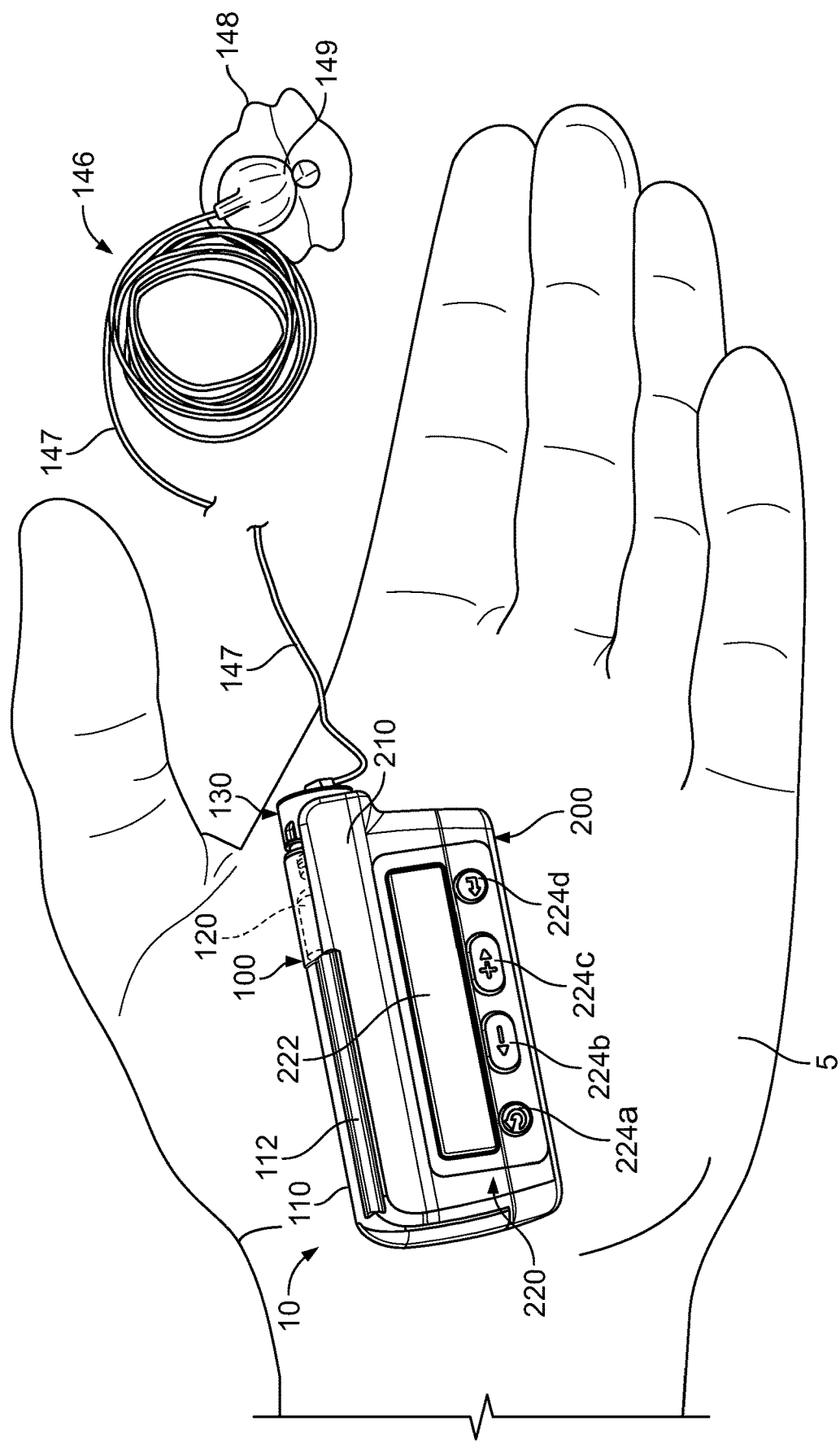
FIG. 6 is a perspective view of an infusion pump system, in accordance with some embodiments.
Figure 9:
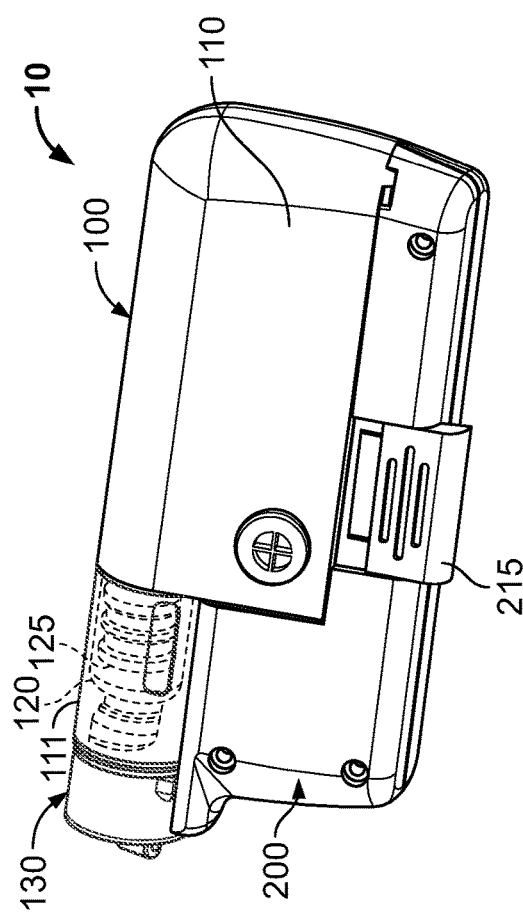
FIGS. 9-10 are perspective views of a pump device being detached from a controller device, in accordance with some embodiments.
Figure 10:
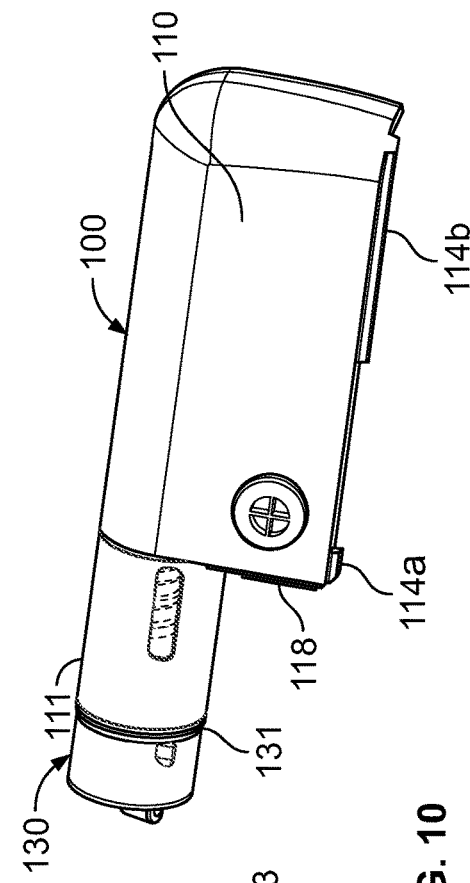
Figure 10:
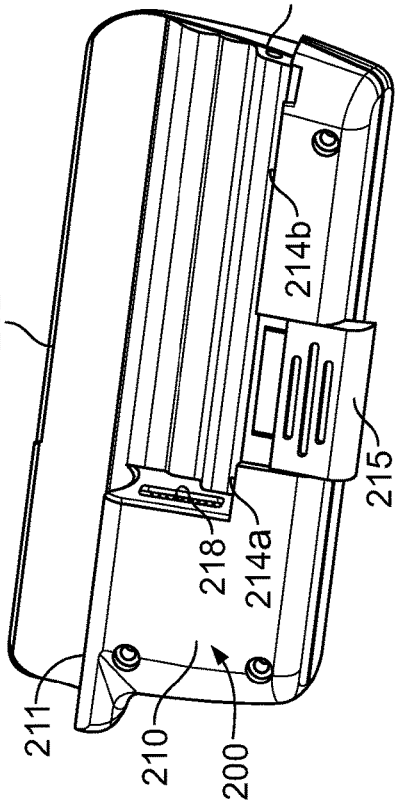

Referring to FIGS. 6-8, the infusion pump system 10 can be configured to be portable and can be wearable and concealable. For example, a user can conveniently wear the infusion pump system 10 on the user's skin (e.g., skin adhesive) underneath the user's clothing or wear the pump device 100 in the user's pocket (or other portable location) while receiving the medicine dispensed from the pump device 100. As described below in connection with FIGS. 16-18, the drive system of the pump device 100 can be arranged in a compact manner so that the pump device 100 has a reduced length. For example, in the circumstances in which the medicine cartridge 120 has a length of about 6 cm to about 7 cm (about 6.4 cm in one embodiment), the overall length of the pump housing structure 110 (which contains medicine cartridge and the drive system) can be about 7 cm to about 10 cm and about 7 cm to about 9 cm (about 8.3 cm or less in some embodiments). In addition, the pump housing structure 110 can have an overall height of about 2 cm to about 4 cm (about 3.1 cm or less in some embodiments) and an overall thickness of about 8 mm to about 20 mm (about 17.5 mm or less in one embodiment).

The pump system 10 is shown in FIG. 6 as being held in a user's hand 5 so as to illustrate an exemplary size of the system 10 in accordance with some embodiments. This embodiment of the infusion pump system 10 is compact so that the user can wear the portable infusion pump system 10 (e.g., in the user's pocket, connected to a belt clip, adhered to the user's skin, or the like) without the need for carrying and operating a separate module. In such embodiments, the cap device 130 of the pump device 100 can be configured to mate with an infusion set 146. In general, the infusion set 146 can be a tubing system that connects the infusion pump system 10 to the tissue or vasculature of the user (e.g., to deliver medicine into the tissue or vasculature under the user's skin). The infusion set 146 can include a flexible tube 147 that extends from the pump device 100 to a subcutaneous cannula 149 retained by a skin adhesive patch 148 that secures the subcutaneous cannula 149 to the infusion site. The skin adhesive patch 148 can retain the infusion cannula 149 in fluid communication with the tissue or vasculature of the patient so that the medicine dispensed through the tube 147 passes through the cannula 149 and into the user's body. The cap device 130 can provide fluid communication between the output end 122 (FIG. 1) of the medicine cartridge 120 and the tube 147 of the infusion set 146.

Referring to FIG. 7, in some embodiments, the infusion pump system 10 can be pocket-sized so that the pump device 100 and controller device 200 can be worn in the user's pocket 6 or in another portion of the user's clothing. In some circumstances, the user may desire to wear the pump system 10 in a more discrete manner. Accordingly, the user can pass the tube 147 from the pocket 6, under the user's clothing, and to the infusion site where the adhesive patch 148 can be positioned. As such, the pump system 10 can be used to delivery medicine to the tissues or vasculature of the user in a portable, concealable, and discrete manner.

Referring to FIG. 8, in some embodiments, the infusion pump system 10 can be configured to adhere to the user's skin 7 directly at the location in which the skin is penetrated for medicine infusion. For example, a rear surface 102 (FIG. 3) of the pump device 100 can include a skin adhesive patch so that the pump device 100 can be physically adhered to the skin of the user at a particular location. In these embodiments, the cap device 130 can have a configuration in which medicine passes directly from the cap device 130 into an infusion cannula 149 that is penetrated into the user's skin. In some examples, the user can temporarily detach the controller device 200 (while the pump device 100 remains adhered to the skin 7) so as to view and interact with the user interface 220.

Referring now to FIGS. 9-14, the infusion pump system 10 can be operated such that the pump device 100 is a disposable, non-reusable component while the controller device 200 is a reusable component. In these circumstances, the pump device 100 may be configured as a "one-time-use" device that is discarded after the medicine cartridge is emptied, expired, or otherwise exhausted. Thus, in some embodiments, the pump device 100 can be designed to have an expected operational life of about 1 day to about 30 days, about 1 day to about 20 days, about 1 to about 14 days, or about 1 day to about 7 days—depending on the volume of medicine in the cartridge 120, the dispensation patterns that are selected for the individual user, and other factors. For example, a medicine cartridge 120 containing insulin can have an expected usage life about 7 days after the cartridge is removed from a refrigerated state and the septum 121 is punctured. In some circumstances, the dispensation pattern selected by the user can cause the insulin to be emptied from the medicine cartridge 120 before the 7-day period. If the insulin is not emptied from the medicine cartridge 120 after the 7-day period, the remaining insulin can become expired sometime thereafter. In either case, the pump device 100 and the medicine cartridge 120 therein can be discarded after exhaustion of the medicine cartridge 120 (e.g., after being emptied, expired, or otherwise not available for use).

The controller device 200, however, may be reused with subsequent new pump devices 100' and new medicine cartridges 120'. As such, the control circuitry, the user interface components, and other components that may have relatively higher manufacturing costs can be reused over a longer period of time. For example, in some embodiments, the controller device 200 can be designed to have an expected operational life of about 1 year to about 7 years, about 2 years to about 6 years, or about 3 years to about 5 years—depending on a number of factors including the usage conditions for the individual user. Accordingly, the user can be permitted to reuse the controller device 200 (which can include complex or valuable electronics) while disposing of the relatively low-cost pump device 100 after each use. Such a pump system 10 can provide enhanced user safety as a new pump device 100' (and drive system therein) is employed with each new fluid cartridge 120.

Referring to FIGS. 11-12, the same controller device 200 can be reused with a new pump device 100' having a new medicine cartridge 120' retained therein, and the previously used pump device 100 can be discarded with the exhausted medicine cartridge 120. The new pump device 100' (FIG. 11) can have a similar appearance, form factor, and operation as the previously used pump device 100 (FIGS. 9-10 and 12), and thus the new pump device 100' can be readily attached to the controller device 200 for controlled dispensation of medicine from the new medicine cartridge 120'. In some embodiments, the user can prepare the new pump device 100 for use with the controller device 200. For example, the user may insert the new medicine cartridge 120' in the cavity 116 of the new pump device 100' and then join the cap device 130 to the pump housing to retain the new medicine cartridge 120' therein (refer, for example, to FIG. 1). Although the tubing 147 of the infusion set 146 is not shown in FIG. 11, it should be understood that the tubing 147 can be attached to the cap device 130 prior to the cap device 130 being joined with the housing 110. For example, a new infusion set 146 can be connected to the cap device 130 so that the tubing 147 can be primed (e.g., a selected function of the pump device 100 controlled by the controller 200) before attaching the infusion set patch to the user's skin. As shown in FIG. 11, the new medicine cartridge 120' may be filled with medicine such that the plunger 125 is not viewable through the barrel 111.

Referring to FIGS. 13-14, the new pump device 100' can be removably attached to the controller device 200 to assemble into the infusion pump system 10 for delivery of medicine to the user. Before the pump device 100 is electrically connected with the controller device 200, the user may prepare the new pump device 100' for use by pulling the removable tab 141 away from the pump housing 110. The new pump device 100' can include the removable tab 141 to seal the battery in the unused pump device 100' and thereby maintain the battery in a storage mode (refer, for example, to FIG. 12 in which the removable tab 141 is arranged to cover an internal face of the vent 115). As described in more detail below, when the new pump device 100' is prepared for usage, the removable tab 141 can be pulled away from the pump housing 110 (and away from the battery therein), which switches the battery into an activation mode. Thus, the shelf-life of the pump device 100' (prior to usage with the controller device 200) may be extended by sealing the battery in a storage mode because little, if any, energy is dissipated from the battery when in the storage mode.

The guided motion in the longitudinal direction 219 provides the user with a convenient "one-movement" process to attach the pump device 100' and the controller device 200. For example, the user can readily slide the pump device 100' and the controller device 200 toward one another in a single movement (e.g., in the longitudinal direction) that causes both a physical connection and an electrical connection. Thus, the infusion pump system 10 can permit users to readily join the pump device 100' and the controller device 200 without compound or otherwise difficult hand movements—a feature that can be beneficial to child users or to elderly users.

Figure 15:
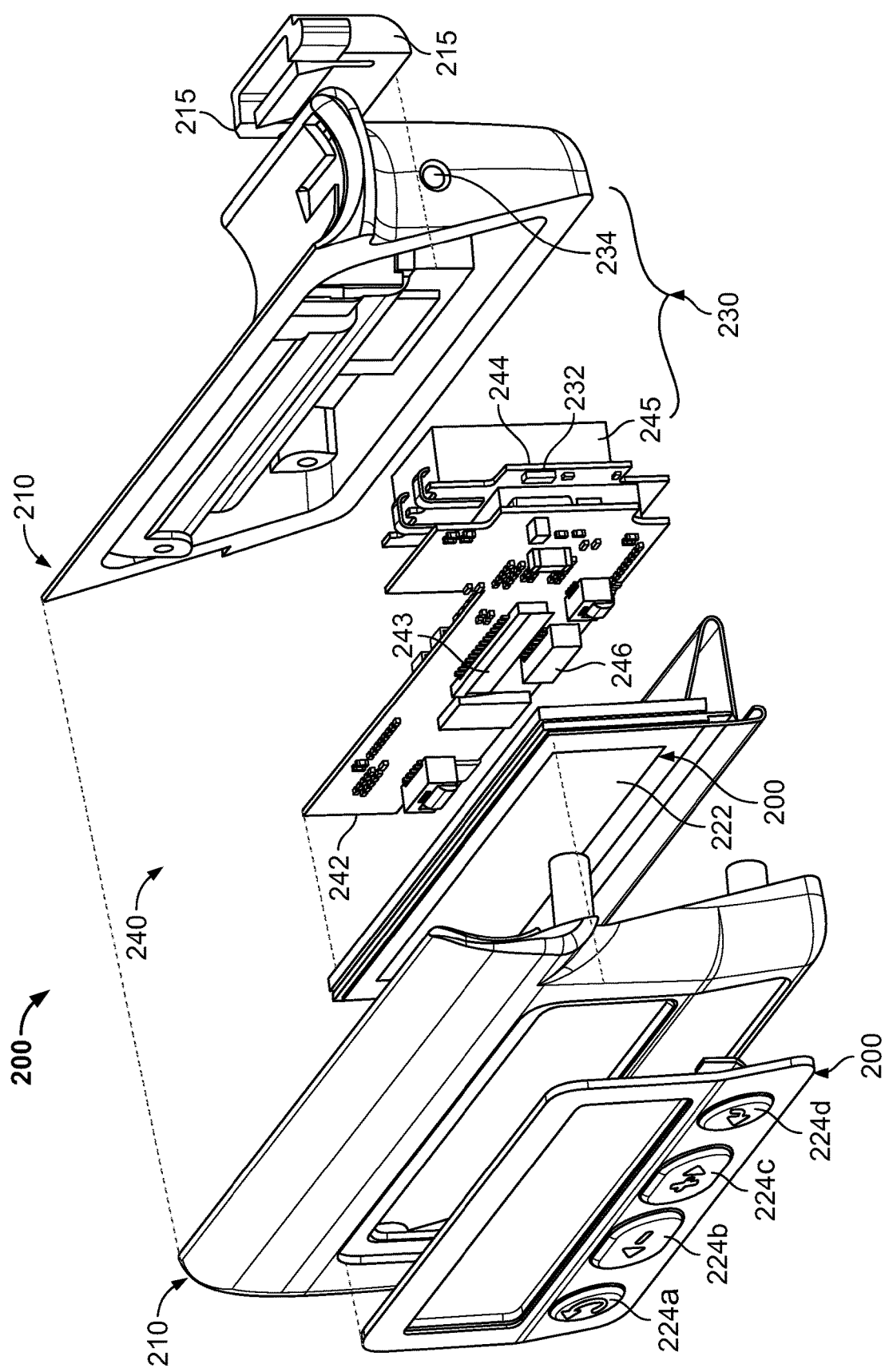
FIG. 15 is an exploded perspective view of a controller device for an infusion pump system, in accordance with some embodiments.

Referring now to FIG. 15, the controller device 200 (shown in an exploded view) houses a number of components that can be reused with a series of successive pump devices 100. In particular, the controller device 200 includes control circuitry 240 arranged in the controller housing 210 that is configured to communicate control signals to the drive system of the pump device 100. In this embodiment, the control circuitry 240 includes a main processor board 242 that is in communication with a power supply board 244. The control circuitry 240 includes at least one processor 243 that coordinates the electrical communication to and from the controller device 200 (e.g., communication between the controller device 200 and the pump device 100). The processor 243 can be arranged on the main processor board 242 along with a number of other electrical components such as memory devices. It should be understood that, although the main processor board 242 is depicted as a printed circuit board, the main processor board can have other forms, including multiple boards, a flexible circuit substrate, and other configurations that permit the processor 243 to operate. The control circuitry 240 can be programmable in that the user may provide one or more instructions to adjust a number of settings for the operation of the infusion pump system 10. Such settings may be stored in the memory devices arranged in the control circuitry 240. Furthermore, the control circuitry 240 may include one or more dedicated memory devices that store executable software instructions for the processor 243.

The control circuitry 240 may include other components, such as sensors, that are electrically connected to the main processor board 242. For example, the activity sensor 246 can be electrically connected to the main processor board 242 so as to communicate movement characteristics data to the processor 243 or other components of the control circuitry 240. The activity sensor 246 may comprise, for example, a motion sensor (e.g., an accelerometer) that is configured to surface mount to the main processor board 242. Also, the activity sensor 246 may comprise an inclination sensor to determine if the user is lying horizontally, rather than standing up or sitting up. In such circumstances, the inclination sensor may be housed with the motion sensor or may comprise a separate housing that is electrically connected to components of the control circuitry. As such, the activity sensor 246 may comprise a single instrument or multiple instruments that are separately joined to the control circuitry.

Still referring to FIG. 15, in some embodiments, the activity sensor 246 can be used to detect and record movement characteristics such as the acceleration of the pump system 10 (e.g., while worn by the user), the vibrations of the pump system 10, the inclination of the pump system 10, or a combination thereof. As described in more detail below in connection with FIGS. 19-22, this movement characteristic information can be processed by the control circuitry 240 of the controller device 200 for purposes of generating alerts or queries to the user. When a period of elevated activity level is sensed (e.g., the activity sensor 246 senses an increased amount of motion), the user can be prompted (e.g., by an audible tone or a visual indication) to respond to a query displayed on the display device 222 of the user interface 220. Exemplary queries can include a prompt asking the user to confirm if he or she is exercising or taking part in an increased amount of activity (refer, for example, to the display device 222 of FIG. 1). Because increased motion of the accelerometer 10 does not necessarily translate to an increased level of physical activity, the controller device 200 can employ these confirmation tools (e.g., querying the user) to determine if actual activity levels of the user have been increased.

It should be understood from the description herein that, in some embodiments, the activity sensor 246 may comprise a collection of sensor instruments beyond the previously described motion sensor. As described in more detail below, the activity sensor can include (in addition to or as an alternative to the motion sensor 246 arranged with the control circuitry 240) a heart rate sensor, a blood pressure sensor, a body temperature sensor, a perspiration sensor, or other instruments to determine if the activity level of the user has increased. Accordingly, in cases where motion is detected by the activity sensor, these additional sensor instruments can be utilized by the controller device 200 to corroborate if the user is exercising or performing an elevated physical activity. In these embodiments where the activity sensor incorporates a number of sensor instruments, the activity sensor may provide enhanced accuracy of the activity estimations and reduce the likelihood of false alerts to the user.

Still referring to FIG. 15, the controller device 200 can be electrically connected with the pump device 100 via mating connectors 118 and 218 (FIGS. 4-5) so that the control circuitry 240 can communicate control signals to the pump device 100 and receive feedback signals from components housed in the pump device 100. In this embodiment, the electrical connector 118 (FIG. 5) on the pump device 100 is a z-axis connector, and the connector 218 (FIG. 4) on the controller device 200 is adapted to mate therewith. The electrical connector 218 on the controller device 200 is in communication with the control circuitry 240. As such, the processor 243 can operate according to software instructions stored in the memory device so as to send control signals to the pump device 100 via the connector 218.

Also as previously described, the controller device 200 can include the illumination instrument 230 that may be operated by the controller circuitry 240. For example, the illumination instrument 230 can include an LED device 232 that is electrically activated by the control circuitry 240 according to the user's input or according to the previously described automated conditions. The light emitted from the LED device 232 can be transmitted through a light guide 234 arranged on the external face of the controller housing 210. It should be understood that, in other embodiments, the illumination instrument 230 may include other light source configurations.

Still referring to FIG. 15, the user interface 220 of the controller device 200 can include input components, output components, or both that are electrically connected to the control circuitry 240. For example, in this embodiment, the user interface 220 includes a display device 222 having an active area that outputs information to a user and four buttons 224a-d that receive input from the user. Here, the display 222 may be used to communicate a number of settings or menu options for the infusion pump system 10. In this embodiment, the control circuitry 240 may receive the input commands from the user's button selections and thereby cause the display device 222 to output a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining the cartridge 120, or the like). As previously described, the controller circuit 240 can be programmable in that the input commands from the button selections can cause the controller circuit 240 to change any one of a number of settings for the infusion pump system 100.

Some embodiments of the control circuitry 240 may include a cable connector (e.g., a USB connection port or another data cable port) that is accessible on an external portion of the controller housing 210. As such, a cable may be connected to the control circuitry 240 to upload data or program settings to the controller circuit or to download data from the control circuitry 240. For example, historical data of medicine delivery can be downloaded from the control circuitry 240 (via the cable connector) to a computer system of a physician or a user for purposes of analysis and program adjustments. Optionally, the data cable may also provide recharging power.

Figure 16:
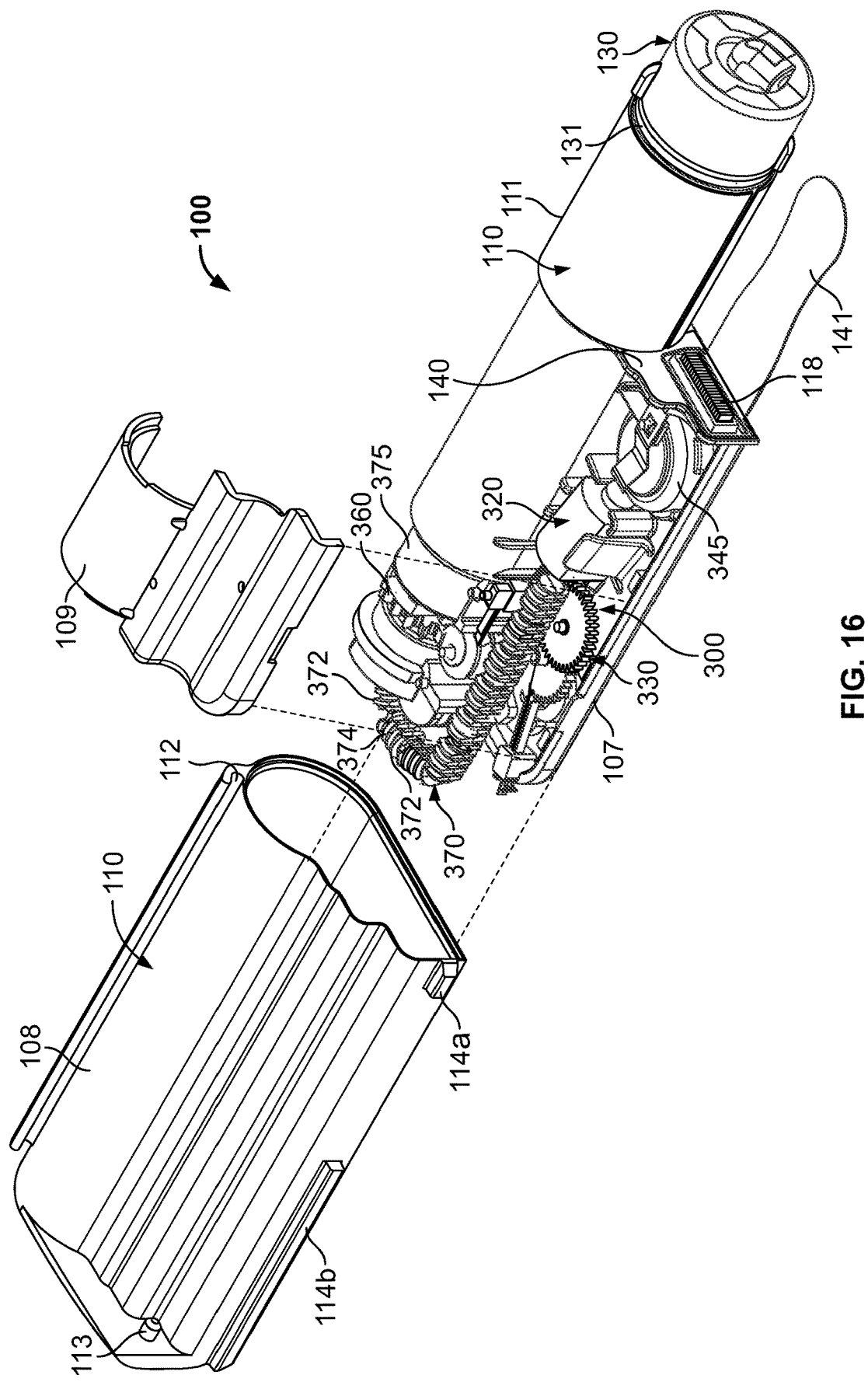
FIG. 16 is an exploded perspective view of a pump device for an infusion pump system, in accordance with some embodiments.

Referring to FIGS. 15-16, the infusion pump system 10 can have two power sources 345 (FIG. 16) and 245 (FIG. 15) that cooperate to power the infusion pump system 10. For example, in some embodiments, the pump device 100 can include a first power source 345 (refer to FIG. 16) capable of transmitting electrical energy to the controller device 200 when the pump device 100 is attached to the controller device 200. The control circuitry 240 of the controller device 200 can include a second power source 245, which can be coupled to the power supply board 244 of the control circuitry 240. The second power source 245 can include a high current-output battery that is capable of discharging a brief current burst to power, for example, a drive system (Refer to FIG. 16) of the pump device 100 and is capable of accepting and storing electrical energy over time and (e.g., "trickle charge"). The hard-wired transmission of electrical energy from the power source 245 to the drive system 300 can occur through the previously described connectors 118 and 218 (FIGS. 4-5). The second power source 245 can receive electrical energy from a power source housed in the pump device 100 (e.g., the first power source 345), from a plug-in wall charger, from a cable connector (e.g., a USB connection port that is connected to the control circuitry 240), or from another charging device (e.g., a charging cradle).

Accordingly, the infusion pump system 10 can have two power sources 345 and 245—one arranged in the disposable pump device 100 and another arranged in the reusable controller device 200—which can permit a user to continually operate the controller device 200 without having to recharge a battery via a plug-in wall charger or other cable. Because the controller device 200 can be reusable with a number of pump devices 100 (e.g., attach the new pump device 100' after the previous pump device 100 is expended and disposed), the second power source 245 in the controller device can be recharged over a period of time, each time when a new pump device 100 is connected thereto. Such a configuration can be advantageous in those embodiments where the pump device 100 is configured to be a disposable, one-time-use device that attaches to a reusable controller device 200. For example, in those embodiments, the "disposable" pump devices 100 recharge the second power source 245 in the "reusable" controller device 200, thereby reducing or possibly eliminating the need for separate recharging of the controller device 200 via a power cord plugged into a wall outlet.

Figure 17:
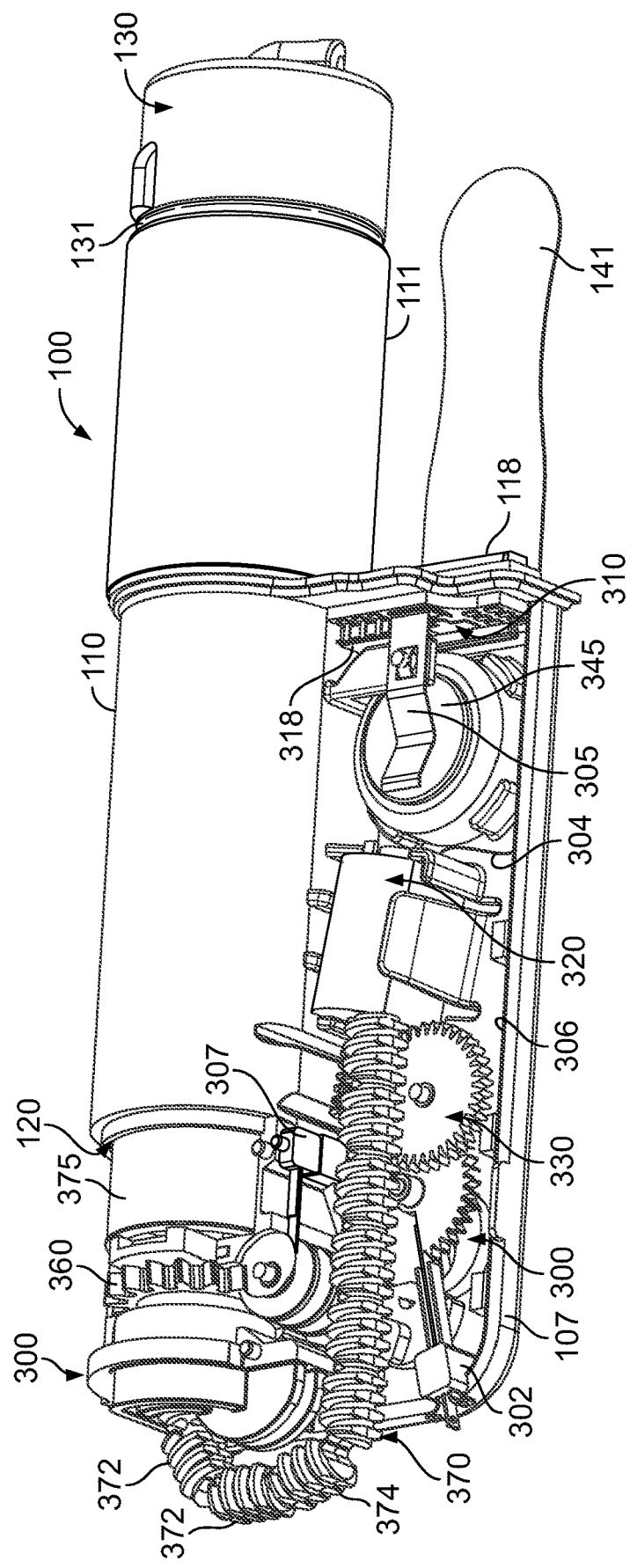
FIG. 17 is a perspective view of a portion of the pump device of FIG. 16.
Figure 18:
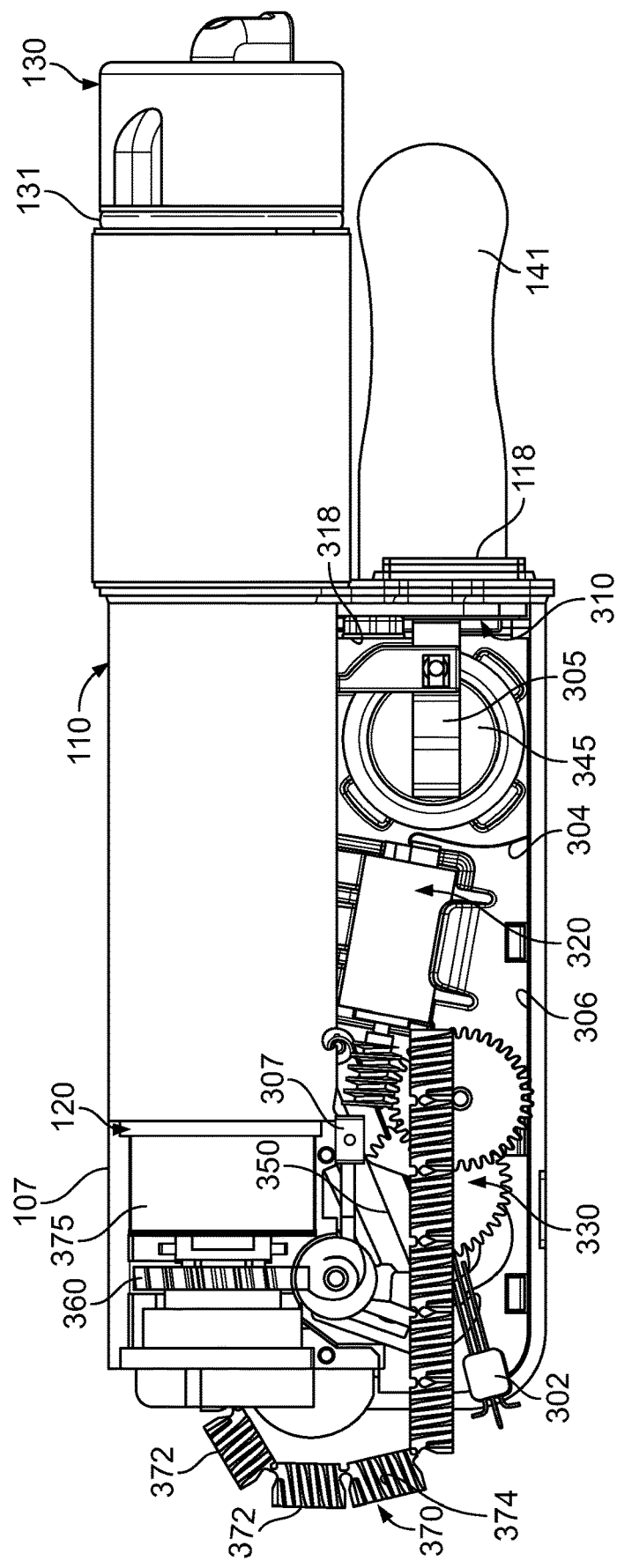
FIG. 18 is a top view of a portion of the pump device of FIG. 16.

Referring now to FIGS. 16-18, the pump device 100 may include a drive system 300 that is controlled by the removable controller device 200 (FIGS. 1-5). Accordingly, the drive system 300 can accurately and incrementally dispense fluid from the pump device 100 in a controlled manner. The drive system 300 may include a flexible piston rod 370 that is incrementally advanced toward the medicine cartridge 120 so as to dispense the medicine from the pump device 100. At least a portion of the drive system 300 is mounted, in this embodiment, to the pump housing 110. In this embodiment, the pump housing 110 includes a chassis 107, a shell portion 108, and a cover mount 109. The shell portion 108 can be used to cover at least a portion of the drive system 300. For example, the shell 108 may include an inner curved surface against which a curved section of a piston rod 370 rests. The cover mount 109 may be assembled to the chassis 107 of the pump housing 110 to secure some components of the drive system 300 in position between the cover mount 109 and the chassis 107. When the cover mount 109 is assembled into place, the "unused" or retracted portion of the piston rod 370 may rest in a channel defined in the top of the cover mount 109. The shell portion 108 can slide over the cover mount 109 and join with the chassis 107 to form the assembled pump housing 110.

Some embodiments of the drive system 300 may include a battery powered actuator (e.g., reversible motor 320 or the like) that resets a ratchet mechanism 330, a spring device 350 (FIG. 18) that provides the driving force to the ratchet mechanism 330, and a drive wheel 360 that is rotated by the ratchet mechanism 330 to advance the flexible piston rod 370 toward the medicine cartridge 120. The operation of the drive system 300 is described in commonly assigned U.S. patent application Ser. No. 11/677,706, which was filed on Feb. 22, 2007 and is incorporated herein by reference.

As shown in FIGS. 17-18, the pump device 100 can include one or more motion detectors coupled with the drive system 300 to provide feedback regarding the operation of the drive system 300. For example, the pump device 100 may include a first motion detector 302 configured as a limit switch that detects when a portion of the ratchet mechanism has reached the limit of its travel and must thereafter stop movement or reverse direction. The operation of the limit switch 302 is described in previously incorporated U.S. patent application Ser. No. 11/677,706. In another example, the pump device 100 may include a second motion detector 307 in the form of a mechanical error switch that indicates whether components of the drive system 300 completed the desired motion for each drive cycle. The operation of the mechanical error switch 307 is also described in more detail in U.S. patent application Ser. No. 11/677,706.

Referring to FIGS. 17-18, the pump device 100 includes a connector circuit 310 to facilitate the transfer of signals to and from the electrical connector 118. As previously described, the electrical connector 118 of the pump device 100 mates with the connector 218 (FIG. 4) of the controller device 200 so that electrical communication can occur between the pump device 100 and the controller device 200. The connector circuit 310 may comprise a generally non-complex circuit 310 that does not include a processor or other relatively high-cost components. In this embodiment, the connector circuit 310 operates as a passageway for the control signals (from the control circuitry 240 (FIG. 15) of the controller device 200) to transmit to the drive system 300 (e.g., to the actuator 320). For example, the reversible motor 320 may be connected to the connector circuit 310 via one or more wires 304. The connector circuit 310 also operates as a passageway for the electrical power from the first battery 345 (FIG. 17) to pass to the controller device 200 for recharging of the second battery 245 (FIG. 15). For example, the first battery 345 may be connected to the connector circuit 310 via one or more power contacts 305. Furthermore, the connector circuit 310 operates as a passageway for feedback signals (e.g., from the motion detectors 302 and 307) to transmit to the control circuitry 240 (FIG. 15) of the controller device 200. For example, the limit switch 302 may be connected to the connector circuit 310 via one or more wires 306 (the one or more wires connecting the mechanical error switch 307 to the connector circuit 310 are not shown in FIGS. 17-18).

In some embodiments, the connector circuit 310 in the pump device 100 includes a memory device 318 that can store data regarding the pump device 100 and its operational history. For example, the memory device 318 of the connector circuit 310 may include a flash memory chip that is configured to store data such as: a unique serial number designated for the pump device 100, a manufacturer identifier code, and a drive cycle counter. The unique serial number designated for the pump device 100 and the manufacturer identifier code may be useful pieces of quality control information that remains with the pump device 100 throughout its shelf-life and operational life. If, for example, a manufacturing error is identified for a particular pump device 100, the unique serial number and the manufacturer identifier code (e.g., a lot code) can be used to promptly identify the manufacturing location and its manufacturing lot.

The drive cycle counter stored in the memory device 318 can be useful for maintaining an accurate estimate of the volume of medicine that remains in the medicine cartridge 120. For example, the number of drive cycles that are required to incrementally advance the plunger 125 and thereby dispense a full medicine cartridge 120 may be a predetermined value (e.g., in some embodiments, 6,300 drive cycles result in full dispensation of a new medicine cartridge). Accordingly, the drive cycle counter stored in the memory device 318 can keep track of the number of drive cycles that have occurred through the operational life of the pump device 100. Each time the motor 320 completes a new drive cycle and incrementally advances the piston rod 370 to dispense some medicine, the controller device 200 can store an updated value for the drive cycle counter stored in the memory device 318. When the updated value stored in drive cycle counter stored in the memory device 318 approaches the predetermined value, the controller device 200 can alert the user that the medicine cartridge is approaching exhaustion. Furthermore, because the memory device 318 is arranged in the pump device 100, the drive cycle counter stored in the memory device 318 remains local to the pump device 100. If the pump device 100 is temporarily disconnected from the controller device 200 and then reconnected (or reconnected to a different controller device 200), the controller device 200 can retrieve the value for the drive cycle counter stored in the memory device 318 and promptly ascertain how much medicine remains in the medicine cartridge 120.

Still referring to FIGS. 17-18, in some embodiments, the flexible piston rod 370 comprises a plurality of segments 372 serially connected by hinge portions 373 so that the flexible piston rod 370 is adjustable from a curved shape to a noncurved shape. The plurality of segments 372 and the interconnecting hinge portions 373 can be integrally formed in one piece from one or more moldable materials, including polymer materials such as Nylon or POM. In this embodiment, each of the plurality of rod segments 372 includes an exterior thread pattern 374 along at least one cylindrical surface portion. The piston rod 370 also includes a plunger engagement device 375 can be arranged at a forward end of the piston rod 370. As such, the plunger engagement device 375 faces toward the medicine cartridge 120 when the medicine cartridge 120 is inserted into the cavity 116. In some embodiments, the plunger engagement device 375 may comprise a pusher disc that abuts against the plunger 125 of the medicine cartridge 120 (FIG. 1).

Turning now to the operation of the activity sensor (FIGS. 1 and 17) for the infusion pump system 10, the activity sensor can be used to collect real-time data related to the user's physical activity for the purpose of modifying the medicine dispensation rate to the user. For example, in the case of a diabetic user receive insulin infusion from the pump system 10, certain levels of exercise can increase the insulin efficiency, which effectively reduces the need for insulin during (and sometimes after) the period exercise. Furthermore, the user's exercise can also activate non-insulin mediated glucose transport pathways, which may increase effective insulin efficiency. As such, the user's blood glucose levels can fall when the muscles demand more glucose (e.g., during exercise), when the insulin becomes more efficient in the blood, or a combination thereof. In particular circumstances, this reduction in blood glucose levels can lead to hypoglycemia. Accordingly, the activity sensor of the infusion pump system can be used to alert the user as to the detection of exercise or movement characteristics, to adjust the insulin dispensation accordingly, or both.

Figure 19:
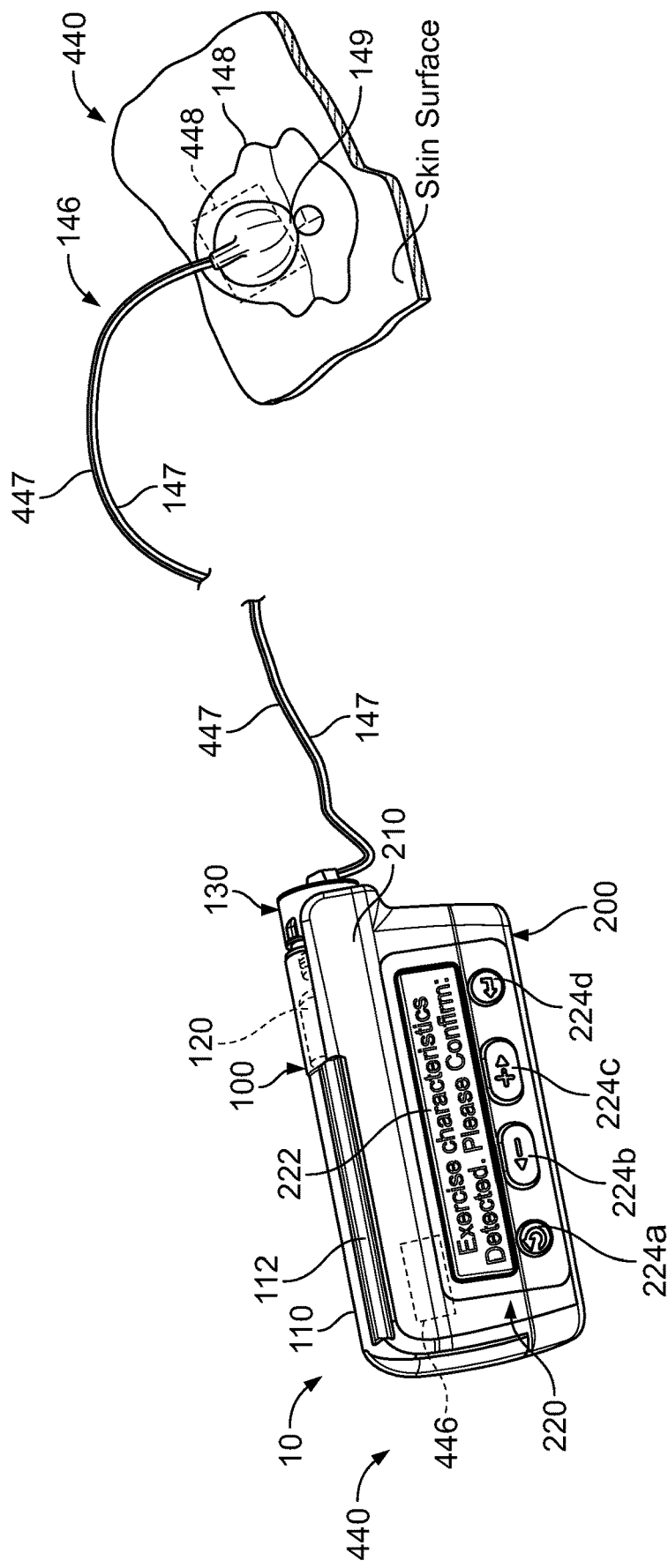
FIG. 19 is a perspective view of an exemplary infusion pump system having an activity sensor.

Referring now to FIG. 19, some embodiments of the activity sensor can operate as a system of sensor instruments that provide data indicate of the user's physical activity. In this embodiment, the activity sensor module 440 includes a motion activity sensor 446 and at least one physiological sensor 448. The motion activity sensor 446 may have a configuration similar to the activity sensor 246 described in connection with FIG. 15. For example the motion activity sensor 446 can be electrically connected to the control circuitry 240 (FIG. 15) so as to communicate movement characteristics data to the one or more components of the control circuitry 240. The motion activity sensor4 may comprise, for example, an accelerometer that is housed in the controller device 200. Also, the motion activity sensor 446 may comprise an inclination sensor to determine if the user is lying horizontally, rather than standing up or sitting up. Thus, the motion activity sensor 446 can be used to detect and record movement characteristics such as the acceleration of the pump system 10 (e.g., while worn by the user), the vibrations of the pump system 10, the inclination of the pump system 10, or a combination thereof.

As shown in FIG. 19, the activity sensor module 440 can also include at least one physiological sensor 448 arranged to detect a physiological parameter of the user while the pump system is carried or otherwise worn by the user. For example, the physiological sensor 448 can monitor parameters associated with increased activity, such as decreased blood oxygen levels, increased blood pressure, increased heart rate, increased core temperature, increased respiration rate, increased perspiration, increased muscle activity, and the like. Such physiological sensors for measuring activity levels could be built into the controller device 200, the pump device 100, the infusion set 146, or into other remote devices suitable for locating in a position on the body that will provide an indication of user activity levels independent of the position of the pump system on the users body (e.g., positioned on a limb, on the torso, or the like). These physiological sensors could transmit raw activity data or processed activity data to the controller device 200 via a direct connection (e.g., optical transmission, electrical transmission, or mechanical transmission) or via telemetry (e.g., RF communications, IR communications, or Ultrasonic communications).

In this embodiment, the physiological sensor 448 is arranged on the infusion set 146 of the pump system 10 so as to engage with a targeted portion of the user's body. The infusion set 146 may include a lead 447 arranged along the tubing 147 so that data signals from the physiological sensor 448 can be communicated to the pump system 10 (e.g., from a thin lead in the cap device 130 that communicates with the electrical connectors 118 and 218 to the control circuitry 240 of the controller device 200 in this embodiment). For example, the physiological sensor 448 may comprise a heart rate sensor arranged on the infusion set 146 so as to detect the user's heart rate when the infusion set 146 is adhered to the user's skin. The heart rate data from the physiological sensor 448 can be communicated to the controller device 200 of the pump system 10 via the lead 447. Thus, the activity sensor module 440 can employ the motion sensor 446 to detect the user's movement characteristics that are indicative of exercise or an elevated physical activity. Also, the activity sensor 440 can detect changes in user's heart rate (e.g., via the physiological sensor 448) to corroborate that the elevated physical activity has indeed occurred. In such circumstances, the controller device 200 may alert the user to the detected physical activity and (in some embodiments) query the user to confirm that such physical activity has occurred. If the user responds and confirms that the physical exercise has occurred, the controller device 200 may controllably adjust the medicine dispensation rate or may prompt the user the manually adjust the medicine dispensation rate.

In other embodiments, the activity sensor module 440 may operate using data only from one or more physiological sensors 448 (e.g., without employing the motion sensor 446). As such, the controller device 200 can be configured to receive data from activity sensor module 440 (from the one or more physiological sensors) and thereafter determine whether the user's physical activity has been elevated to a threshold exercise level. Such a determination can be based on factors such as decreased blood oxygen levels, increased blood pressure, increased heart rate, increased core temperature, increased respiration rate, increased perspiration, increased muscle activity, and the like. It should be understood from the description herein that the physiological sensor 448 may comprise one or more of a blood oxygen sensor, a blood pressure sensor, a heart rate sensor, a body temperature sensor, a respiration rate sensor, a perspiration sensor, and a muscle activity sensor.

In some embodiments, the pump system 10 can also gather information about a user's activity level from the user interface 220 (e.g., by prompting the user to indicate the amount of physical activity after detection, by the user inputting an amount of physical activity before it begins, or the like). This information of a users activity level permits the control device 200 to determine the adjusted amount of medicine that will be administered to the user (e.g., setting the basal rate, determining bolus size, and the like).

Figure 20A:
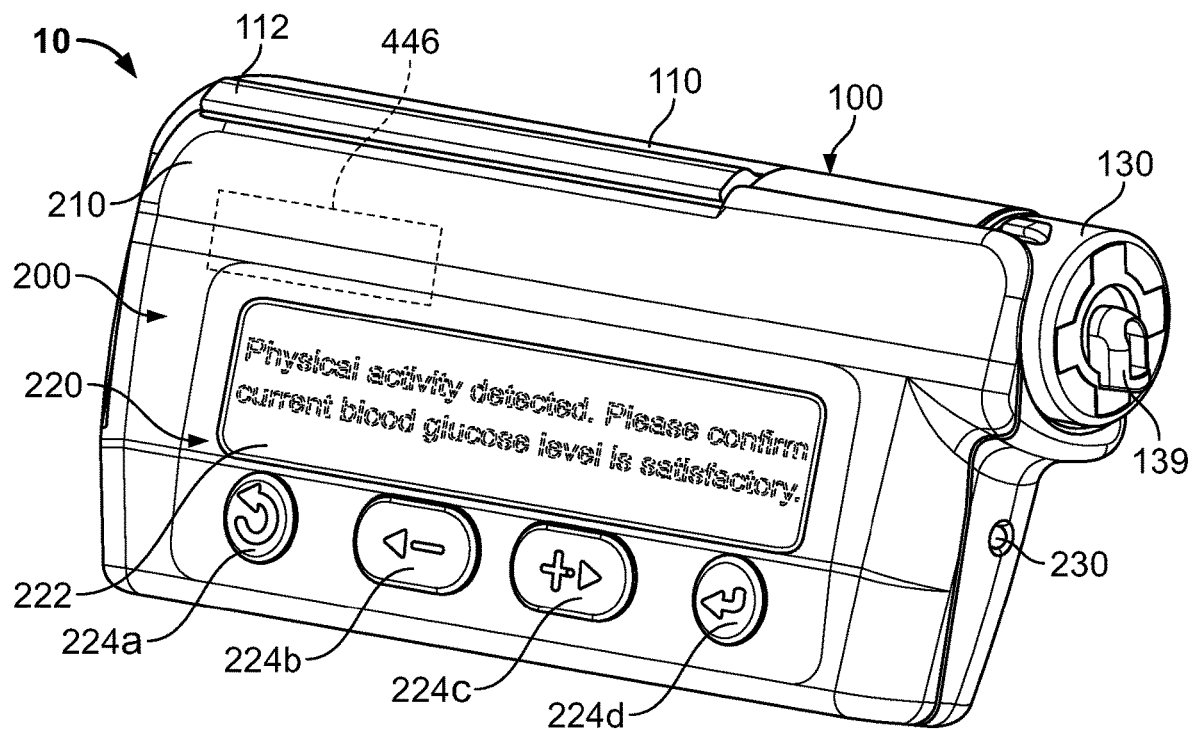
FIGS. 20 A-D are perspective views of the infusion pump system of FIG. 19 displaying an alert.
Figure 20B:
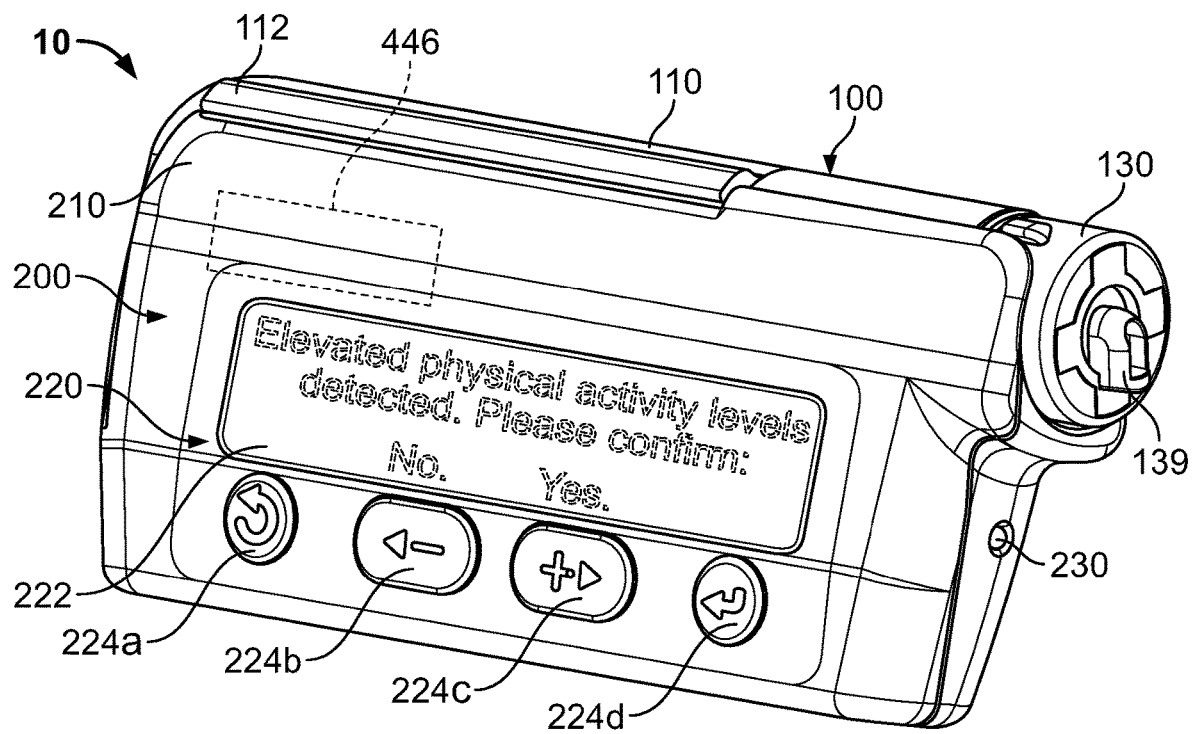
Figure 20C:
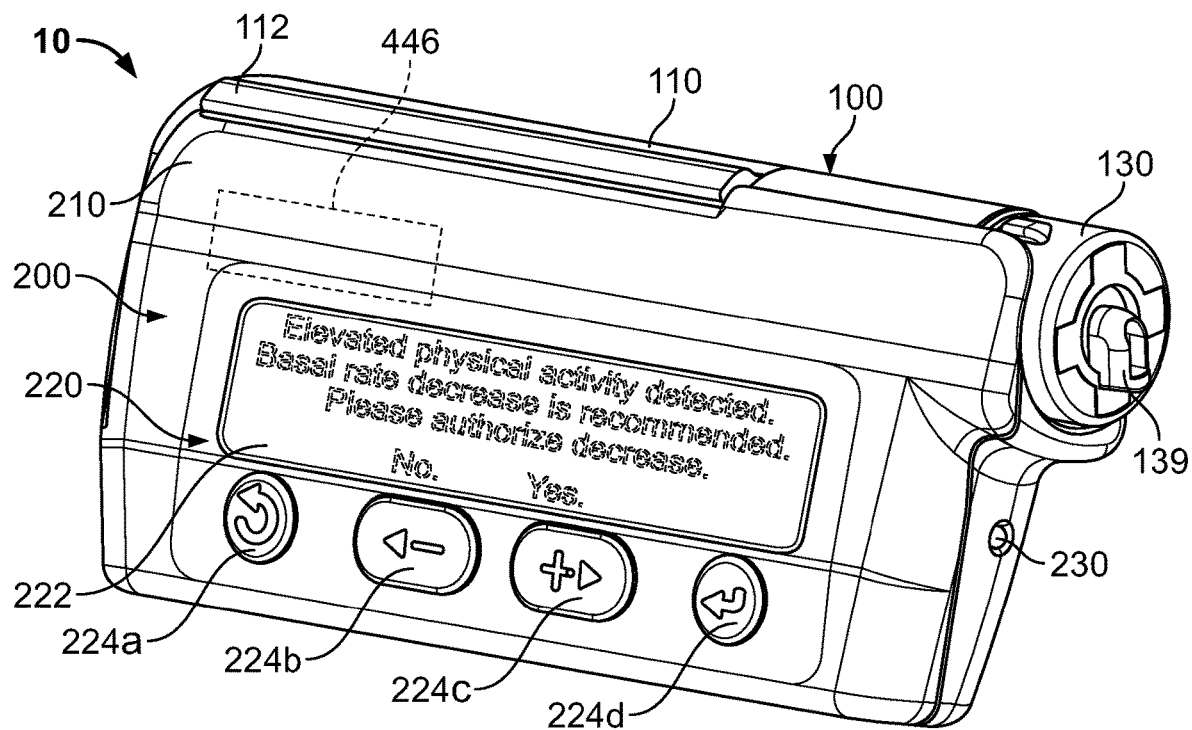
Figure 20D:
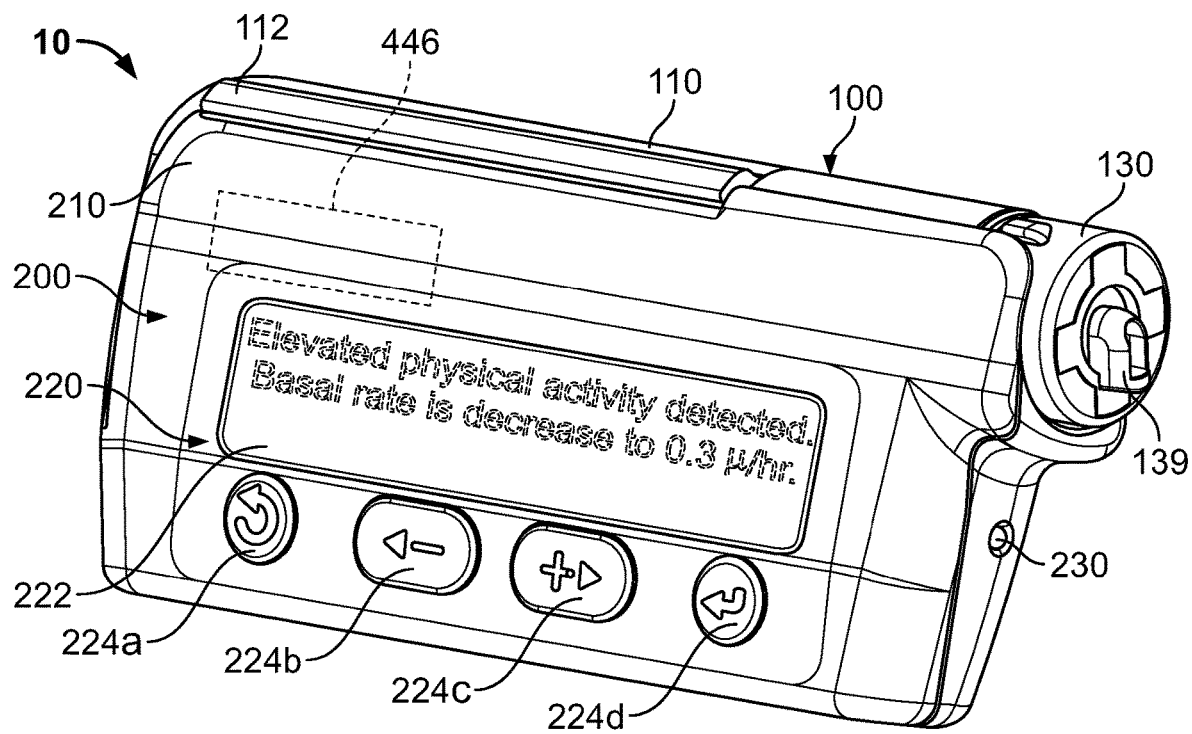

Referring to FIGS. 20A-D, the pump system 10 can respond to an increased activity level of the user in a number of ways. As shown in FIG. 20A, one exemplary response to a detected increase in physical activity can include alerting the user to take more frequent blood glucose measurements or to confirm that the current glucose level is within a satisfactory range. As shown in FIG. 20B, another exemplary response to a detected increase in physical activity can include querying the user about the increased activity (e.g., to confirm that the sensed increase is accurate). As shown in FIG. 20C, another exemplary response to a detected increase in physical activity can include requesting the user to authorize a decrease in insulin delivery. As shown in FIG. 20D, a further exemplary response to a detected increase in physical activity can include automatically decreasing insulin delivery and then alerting the user to the automatic adjustment.

Figure 21A:
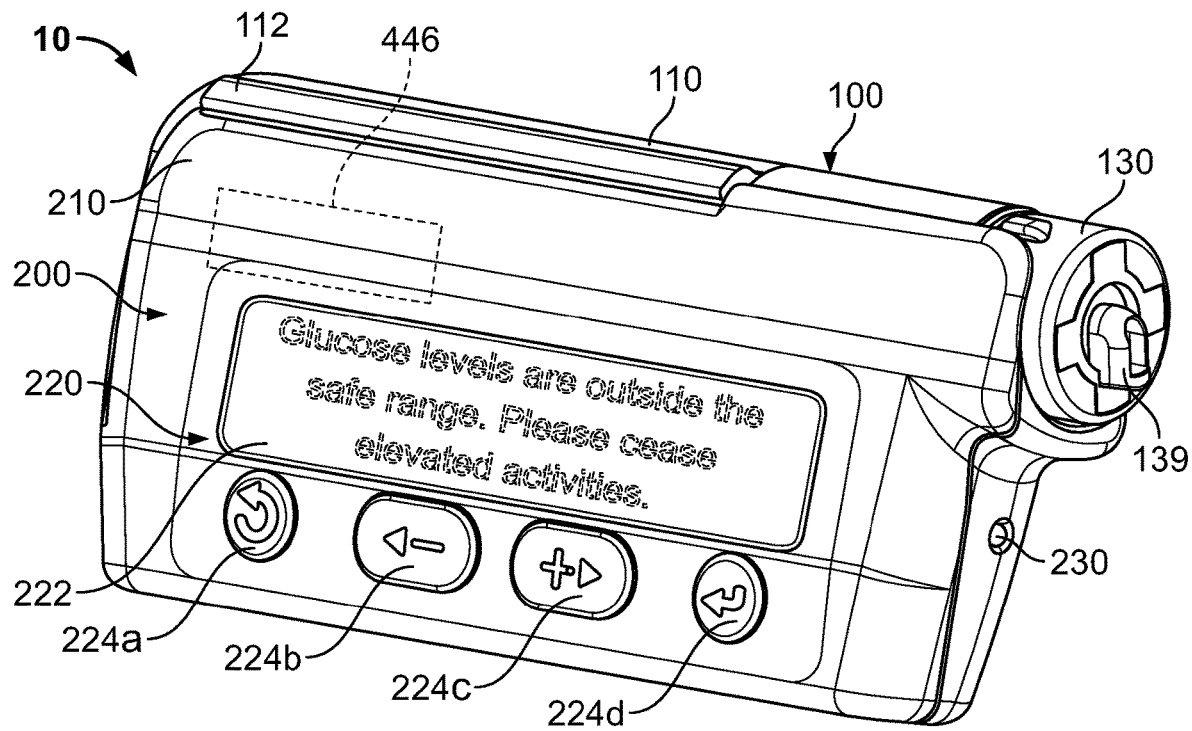
FIGS. 21 A-B are perspective views of the infusion pump system of FIG. 19 displaying an alert.
Figure 21B:
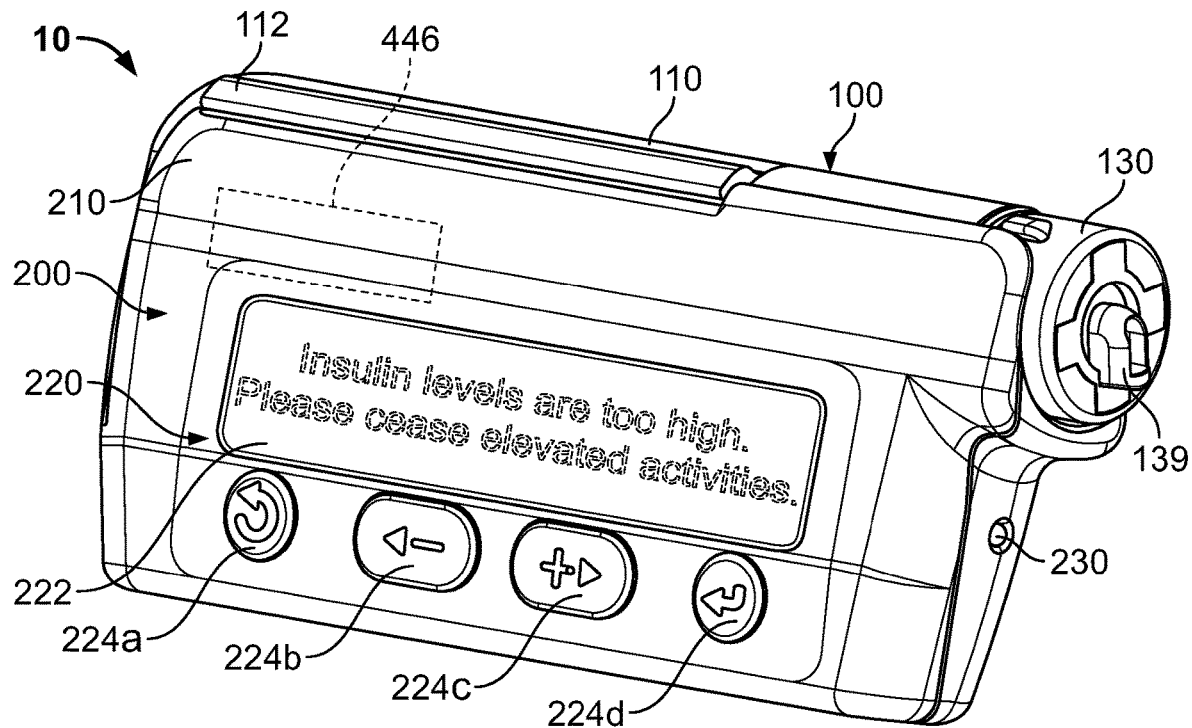

Referring to FIGS. 21A-B, some embodiments of the pump system can be configured to respond to an increased activity level of the user by alerting the user to cease the detected activity. Because exercise is not recommended when blood glucose levels are too low or too high, the pump system 10 can warn the user against continued exercise if high activity levels are detected when blood glucose levels are outside a recommended range. Alternatively, exercise is not recommended insulin levels are too high, so the pump system 10 can also warn the user against continued exercise if high activity levels are detected when insulin levels are predicted to be high (e.g., after a bolus of insulin). In addition, or in the alternative, the pump system 10 could, based on predicted insulin levels and/or blood glucose levels, suggest the user consume an amount of carbohydrates.

In some embodiments, the information gathered from the motion activity sensor 446, the physiological sensor 448, or both can be stored in a log that records the detected physical activity characteristics and particular times and dates. For example, as previously described in connection with FIG. 15, the controller device 200 may be configured to stored such an activity log and other data in the memory devices arranged in the control circuitry 240. This recorded data can be used by the controller device 200 to provide adjustments to the medicine dispensation rate (e.g., to adjust daytime basal rates if low physical activity is detected), to provide corrections to a bolus estimate calculation, or to provide other corrections and adjustments. In such embodiments, the controller device 200 can be configured to receive input from the user via the user interface 220 that permits the user to identify periods of inactivity to ignore. For example, the user may instruct the controller device 200 to ignore a period of inactivity when the user detaches the pump device 100 from the controller device 200 or when the user indicates that he or she is going to sleep for the night. In addition, the controller device 200 can be configured to receive instructions from the user to ignore periods of activity. For example, the user may instruct the controller device to ignore periods of movement activities caused by outside factors such as travel over rough roads, amusement park rides, or pump system manipulation and handling.

Accordingly, the pump system 10 can store data (e.g., regarding blood glucose levels, exercise activity levels, and the like) in the computer readable memory and use this data to adjust the medicine dispensation (e.g., basal rate of insulin delivery, amount of insulin bolus, and the like). Depending on a plurality of factors (e.g., genetics, general health, fitness level, and the like), the user's blood glucose levels may respond differently to a given amount of exercise. Thus, the controller device 200 can maintain a record of a user's blood glucose levels and the activity levels (e.g., detected by the activity sensor module 440) that correspond to these blood glucose levels. This data, in place of or in addition to other data (e.g., food type and amount consumed, and the like) can be used to determine the future responses of the pump system 10 (e.g., adjustment of insulin delivery, and the like) to increased user activity. In some embodiments, a user specific activity ratio can be calculated (e.g., from activity data, blood glucose data, and the like) which would indicate how much a user's blood glucose changes with an increase in activity. In some embodiments, an activity ratio can also indicate how insulin sensitivity changes with activity.

It should be understood that the blood glucose data stored by the controller device may be entered by the user in response to a request for a blood glucose test. For example, as previously described in connection with FIG. 20A, the pump system 10 can request that the user perform a blood glucose measurement when the activity sensor 246 or 446 detects an increased activity level of the user. Because increased activity can be associated with a change (e.g., decrease) in blood glucose level, exercise can cause a drop in blood glucose level that leads to hypoglycemia. The pump system 10 described herein can provide alerts to the user to maintain frequent testing of blood glucose levels during and after exercise, which can help to avert such hypoglycemia conditions. In the circumstances I which the user's blood glucose levels fall (e.g., due to exercise) and the pump system 10 detects or otherwise receives the blood glucose information (e.g., through input by the user), the pump system 10 can make the determination to modify the insulin delivery schedule (e.g., decrease the basal rate, decrease an insulin bolus, or the like). Additionally, the pump system 10 can store data related to the activity level of the user (e.g., as detected by the activity sensor) and the blood glucose level (e.g., as tested by the user). This stored data can be used in a retroactive analysis to determine an appropriate reduction in insulin delivery for a given increase in activity level.

In some embodiments, the pump system 10 can modify the alerts from the user interface 220, the medicine dispensation schedule, or a combination thereof based on a determination that the user is sleeping. For example, the activity sensor 246 or 446 may indicate to the controller device 200 that the user is lying horizontally as opposed to standing or sitting up. Furthermore, the internal clock of the of the controller device 200 may indicate that the time is currently within the user's selected sleep range. As such, the controller device 200 may be configured to decrease the medicine delivery (e.g., decrease basal rate) when the user is sleeping to help avoid nocturnal hypoglycemia. Furthermore, the controller device 200 can be configured to delay certain alerts (e.g., to test blood glucose level) until a later time after the user awake and upright, or to signal an alert based on the amount of time a user has lying in the horizontal position (e.g., signal an alert when the user has been in a horizontal orientation for more than 8 hours, for more than 9 hours, or for more than 10 hours). Such an alert may be used to awaken the user and request that the blood glucose level be tested.

Additionally, in some embodiments, the pump system 10 can be configured to monitor for movement and physiological characteristics that are indicative of a seizure (e.g., which can occur in the event of hypoglycemia). For example, as previously described, the activity sensor 246 or 446 may indicate to the controller device 200 that the user is lying horizontally as opposed to standing or sitting up. In addition, the activity sensor 246 or 446 can be used to detect vibration movements or other motion patterns of the user that are indicative of a seizure event while the user is in a horizontal orientation. In such circumstances, the pump system 10 can respond by stopping the infusion of the insulin or other medicine, communicating an alert (e.g., an audible alarm), displaying information on the display 222 (e.g., a notice requesting that the user check his blood glucose or a notice to a first responder), or a combination thereof.

The activity sensor 246 or 446 permits that the pump system 10 to predict an imminently undesirable or dangerous situation and to thereafter alert the user to take preventative measures. For example, as previously described in connection with FIGS. 21A-B, the pump system 10 can request that the user ceases exercising when the stored data and the senor information indicates that the blood glucose level is outside a safe range or that the insulin level is too high. As such, in circumstances in which the blood insulin levels are predicted by the controller device 200 to be high (e.g., after receiving an insulin bolus), the pump system 10 can be configured to warn the user against further strenuous activity.

In one scenario, a test of the user's blood may indicate an elevated blood glucose level. After the controller device 200 receives this information via the user interface 220, the control circuitry can be used to determine that a bolus of insulin is necessary to lower the blood glucose levels to an acceptable range. Accordingly, the controller device 200 can query the user to confirm that it is acceptable to administer an insulin bolus. When the user can indicate that this is acceptable (e.g., via one of the user selectable buttons 224), the controller device 200 can send control signals to the drive system 300 of the pump device 100 to cause the delivery of the bolus. If the activity sensor 246 or 446 detects an increased level of activity within a short period of time after the bolus delivery (e.g., about five to about thirty minutes later, about ten minutes later, or the like), the controller device 200 can alert the user to cease the activity or the controller device 200 may query the user to confirm that the increased activity level has occurred. The user can confirm, via the user selectable buttons 224, that the increased motion is in fact due to an actual increase in activity level of the user. After receiving such a confirmation from the user, controller device 200 can alert the user to cease the activity (e.g., due to the threat of low glucose levels or hypoglycemia). This alert can be communicated via the display device 222 and may be accompanied by an audible alarm which must be acknowledged by the user (e.g., by pressing one or more of the user selectable buttons 224). If the activity sensor 246 or 446 continues to detect exercise or other elevated physical activities, the controller device 200 can be configured to request that the user performs additional blood glucose test, to cause the pump system 10 to reduce insulin delivery, or a combination thereof. It should be understood from the description herein that this previously described scenario describes on exemplary set of events associated with exercise following a bolus of insulin, but other scenarios can occur where the pump system 10 serves to protect the user against exercise-induced hypoglycemia.

In some embodiments, the pump system 10 can be configured to recommend if it is safe for the user to participate in a future exercise or elevated activity. For example, the blood glucose data, the insulin delivery data, and the activity sensor data sotred by the controller device 200 can be used in a predictive model to estimate the current blood glucose level of the user. If the controller device 200 determines that the blood glucose level is too high (e.g., greater than 300 mg/dl) or too low (e.g., less than 100 mg/dl) for the user to engage in exercise, the controller device 200 can be used to provide a recommendation to the user regarding future planned activities. For example, if the blood glucose level is too low preceding the planned exercise, the increase in physical activity can further lower blood glucose level and possibly lead to hypoglycemia. In the case where the blood glucose level is too high, the short term spike in blood glucose level associated with the beginning of exercise could possibly lead to hyperglycemia. Thus, when a user indicates that a future exercise activity is planned, the controller device 200 can be configured to estimate the current blood glucose level, insulin level, or both. If the blood glucose level determined to be too low (e.g., less than 100 mg/dl), the controller device 200 may communicate an alert that instructs the user to not participate in the planned activity or to consume a certain amount of carbohydrates (e.g., based on the blood glucose level, the physical attributes of the user, the previous responses of the user's blood glucose level to food, and the like). In addition, the controller device 200 can decrease the insulin dispensation rate to the user (e.g., decrease the basal rate, stop the basal injection for a period of time, and the like) in manner that increases the user's blood glucose level before the start of the planned activity. In some circumstances, the controller device 200 can output an alert that notifies the user to not participate or cease exercise and to retest the blood glucose level again after a certain period of time (e.g., 10 minutes to about 1 hour, 15 minutes to about 45 minutes, or about 30 minutes). Conversely, if the blood glucose level is determined to be too high (e.g., greater than 300 mg/dl), the controller device 200 can query the user to increase the insulin dispensation rate or can communicate control signals to the pump device 100 to increase the insulin dispensation rate to the user (e.g., increase the basal rate, dispense a bolus of insulin, and the like) without the user's authorization.

In some embodiments, other techniques can be used to determine the activity level of the user, either alone or in combination with the activity sensor 246 or 446. In some embodiments, a detected change in activity level sensed by the activity sensor 246 or 446 can cause the controller device 200 to prompt the user to manually enter (e.g., using the user interface 220) a particular level of activity. The user can also preemptively enter an activity level. In one example, whenever the user changes his activity level, the user can enter this information into the user interface 220 by selecting from a menu consisting of general activity levels (e.g., low, medium, high, and the like) and/or specific activities (e.g., walking, running, weight-lifting, aerobics, and the like). The controller device 200 can prompt the user to enter information whenever the level activity changes (e.g., when the user begins a walking exercise or the like). Furthermore, the controller device 200 can be equipped to receive user input regarding previous changes in activity level. For example, a user may start exercising at 2:00 PM, but realize at 2:45 PM that he or she forgot to input the start time of his increased activity. The user can enter the type of activity and the start time of his exercise either as an absolute start time (e.g., started at 2:00 PM), as a relative time (e.g., started 45 minutes ago), or the like. As previously described, such data can be stored by the controller device 200, for example, in the memory devices of the control circuitry 240.

Figure 22:
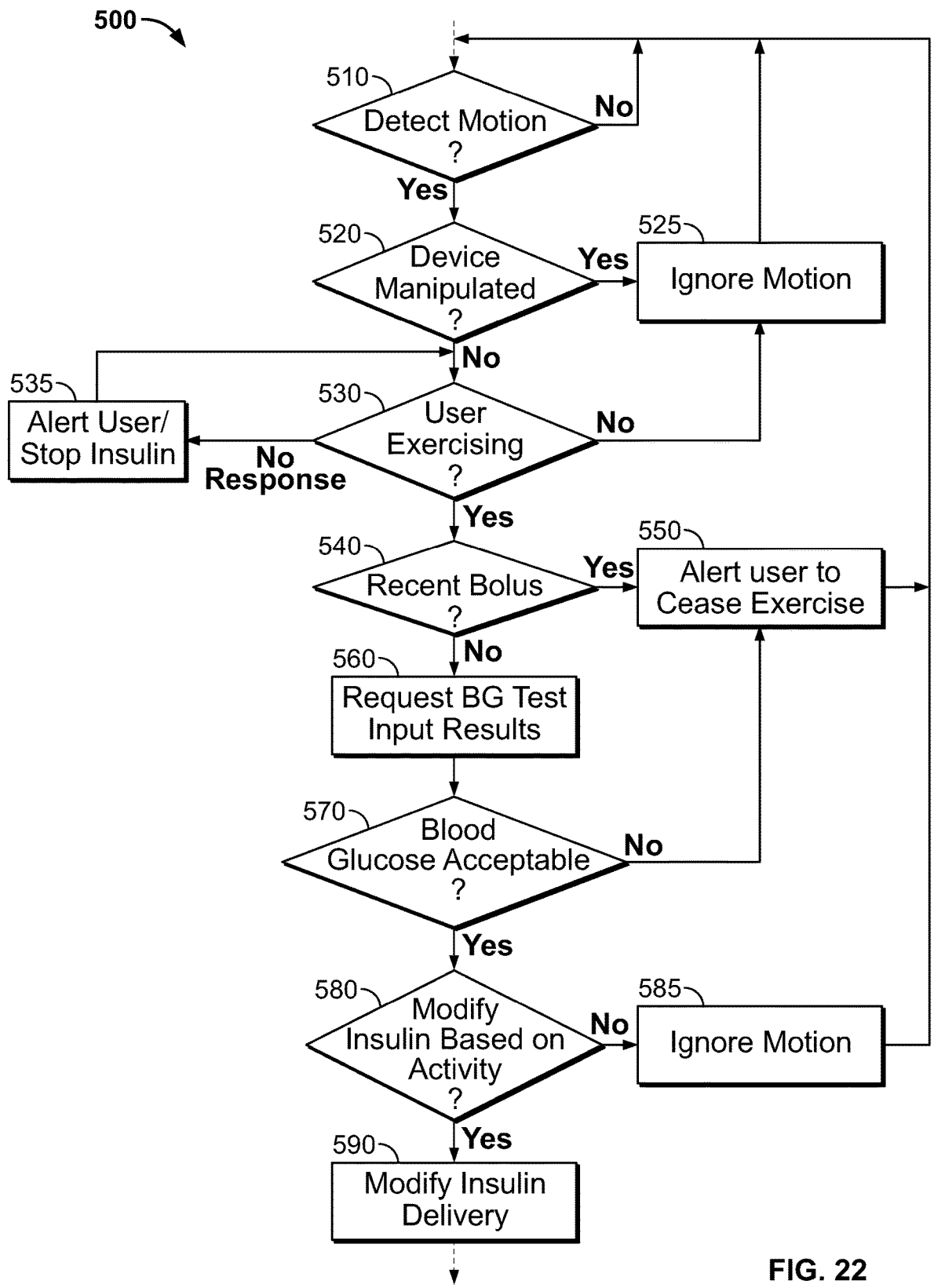
FIG. 22 is a flow chart depicting an exemplary set of steps involving activity detection.

FIG. 22 is a flow chart depicting an exemplary decision making process 500 associated with detection of a possible increase in activity of a user wearing the pump device 10. As described in previous embodiments, the pump device 10 can be equipped to detect movement characteristics (refer to stage 510) or to detect physiological parameters (e.g., an increase in blood pressure, increase in heart rate, increase in body temperature, or the like). In some circumstances, the detected movement characteristics may be caused by event unrelated to the user's exercise (e.g., due to the user detaching the controller device 200 from the pump device 100, due to the user manipulating the pump system 10 in his or her hands, or other such events). As such, the process 400 can include a stage 520 to determine if the user is in the process of or has manipulated the pump system 10 (e.g., such as replacing the pump system 100 with a new one). If the user has manipulated the pump system 10, the process stage 525 can ignore the increased motion detection for a particular period of time (e.g., until the manipulation has ceased, or for a period of about five minutes after the manipulation has ceased) before returning to stage 510 (e.g., monitoring for increased activity). If no manipulation of the device has been recorded (e.g., no detachment of the pump device 100 or no buttons 224 being pushed), the controller device 200 can query the user (refer to stage 530) through the user interface 220 to confirm that the user has increased his or her activity level. If the user responds that no increased activity has occurred, the process can enter stage 525 so as to ignore the detected increase in motion activity for a period of time (e.g., about 5 minutes) before returning to the monitoring stage 510. If the user does not respond to the query of stage 530 (e.g., after a particular timeout period), stage 535 can alert the user (e.g., with a constant audible alarm, message on the display device 222, and the like) and/or suspend insulin delivery until such a time as the user responds to the query of stage 530. For example, an increase in activity level coupled with a non-responsive user can be an indication of nocturnal hypoglycemia.

If the user responds to the query of stage 530 to confirm that he or she has increased the level of physical activity, the controller device 200 can determine (at stage 540) if an insulin bolus has been given recently (e.g., within the last 30 minutes). As exercise in conjunction with high insulin levels can lead to a dangerous drop in blood glucose levels, a bolus of insulin given shortly before or during exercise can cause the controller device 200 to alert the user (at stage 550) that the exercise should be halted. After a period of time (e.g., about 1 minute to about 5 minutes), the pump system 10 can return to monitoring activity levels (e.g., return to stage 510). If the user has not recently received a bolus of insulin, the controller device 200 may request that the user perform a blood glucose test and input the blood glucose test results (at stage 560). The controller device 200 can receive the blood glucose data that thereafter determine (at stage 570) if the blood glucose level of the user is within an acceptable range for exercise acitivities (e.g., greater than about 100 mg/dl and less than about 300 mg/dl). If the blood glucose level is not within the acceptable range, the controller device 200 can alert the user that exercise could should be halted (at stage 550). After a period of time (e.g., about 1 minute to about 5 minutes), the pump system 10 can return to monitoring activity levels (e.g., return to stage 510). If the blood glucose level is determined to be within an acceptable range (e.g., by stage 570), the controller device 200 can query the user (at stage 580) for permission to modify insulin delivery to the user. If the user responds that the adjustment to the insulin delivery is not necessary, the process 400 can continue to stage 485 where the pump system 10 ignore the increased activity for a period of time (e.g., about 5 minutes to about 15 minutes) before returning to monitoring stage 510. If the user responds positively to the query from stage 580, the controller device 200 can modify the insulin dispensation rate (at stage 590) to the user (e.g., lower basal rate, stop basal infusion, lower bolus amount, and the like).

In some embodiments, the controller device 200 can adjust an insulin delivery rate (or basal rate) by a variable amount in response to user input confirming an activity level. In other embodiments, the controller device can switch between two or more preselected basal rate profiles based on a user confirmed activity level. In some embodiments, the controller device 200 can switch between a first and a second preselected basal rate profile after the user has confirmed an activity level and can smoothly transition between the two profiles.

It should be understood from the description herein that, in some embodiments, the activity sensor can be arranged in medical devices other that the wearable infusion pump system 10. For example, medical devices for the treatment of diabetes that are carried or otherwise worn by the user can incorporate an activity sensor to detect and record activity characteristics. Such data can be used to modify insulin dosage calculations or to provide a retrospective summary of the user's activity levels and glucose/insulin level.

Figure 23:
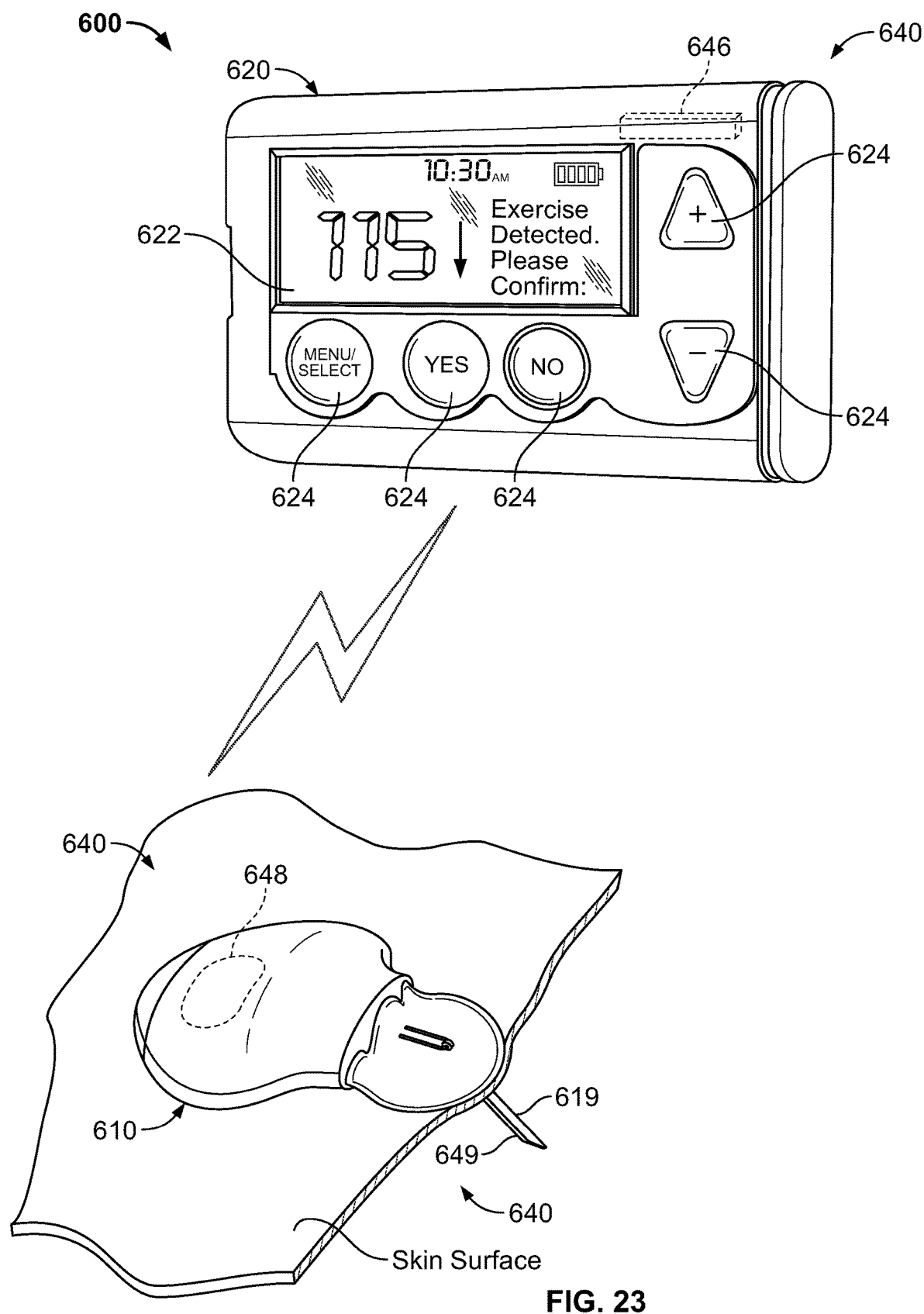
FIG. 23 is a perspective view of a glucose monitor having an activity sensor.

Referring to FIG. 23, some embodiments of a continuous glucose monitoring system 600 can be equipped with an activity sensor module 640 so as to detect and record the user's activity characteristics. The activity sensor module 640 can communicate with the controller 620 of the continuous glucose monitoring system 600 so as to provide indication (e.g., numerically presented or graphically presented) to user of recent activity levels via the user interface 622. Furthermore, the activity sensor module 640 can record the activity data and thereafter provide a retrospective log of activity characteristics that can be reviewed for use in fine tuning or correcting the insulin dosages. Such a review of the log of activity characteristics can be communicated to the user or a medical practitioner using the continuous glucose monitoring system 600 or a remote device (e.g., computer, PDA, cell phone or other device) after downloading the log data to the remote device.

As shown in FIG. 23, the continuous glucose monitoring system 600 includes a body-worn glucose sensor device 610 that wirelessly communicates with a portable controller device 620. The glucose sensor device 610 may comprise a sensor shaft 619 that penetrates under the skin (e.g., into the subcutaneous layer) while the sensor housing is adhered to the skin. The sensor housing may contain a power source and a communication circuit (not shown in FIG. 23) that permits the sensor data to be wirelessly transmitted to controller device 620. The controller device 610 can include a display 622 to communicate the sensed glucose level and one or more buttons 624 for user interaction. In this embodiment, the glucose sensor device 610 also includes one or more physiological sensors 648 and 649 arranged to detect one or more physiological parameters of the user while the glucose sensor device 610 is worn by the user. These physiological sensor 648 and 649 are part of the activity sensor module 640 that is used to detect and record the user's activity characteristics. For example, the physiological sensors 648 and 649 can monitor parameters associated with increased activity, such as decreased blood oxygen levels, increased blood pressure, increased heart rate, increased core temperature, increased respiration rate, increased perspiration, increased muscle activity, and the like. The data signals from the physiological sensors 648 and 649 can be wirelessly communicated to the controller device 620 using the communication circuit of the glucose sensor device 610.

In this embodiment, the physiological sensors 648 can be arranged in the housing of the glucose sensor device 610 so as to contact the user's body when the glucose sensor device 610 is in operation. For example, the physiological sensor 648 may comprise a heart rate sensor that detects the user's heart rate when the glucose sensor device 610 is adhered to the user's skin. Also in this embodiment, the second physiological sensors 649 can be arranged along the sensor shaft 619 of the glucose sensor device 610 so as to penetrate into the user's body when the glucose sensor device 610 is in operation. For example, the second physiological sensor 649 may comprise a blood oxygen sensor, a blood pressure sensor, a body temperature sensor, or another device that detects a physiological parameter indicate of physical activity. As previously described, the physiological sensor data from the physiological sensors 648 and 649 can be communicated to the controller device 620 for processing by the sensor activity module 640 or other control circuitry.

Still referring to FIG. 23, the activity sensor module 640 can also include a motion activity sensor 646 that is capable of detecting physical movement characteristics of the user while the continuous glucose monitoring system 600 is in operation. For example, the motion activity sensor 646 may comprise an accelerometer that is connected to the controller device 620 of the continuous glucose monitoring system 600. Thus, the activity sensor module 640 can employ the motion sensor 646 to detect the user's movement characteristics that are indicative of exercise or an elevated physical activity. Also, the activity sensor module 640 can detect physiological changes via the physiological sensors 648 and 649 to corroborate that the elevated physical activity has indeed occurred. Such a determination can be based on factors such as decreased blood oxygen levels, increased blood pressure, increased heart rate, increased core temperature, increased respiration rate, increased perspiration, increased muscle activity, and the like.

In such circumstances, the controller device 620 may alert the user to the detected physical activity and (in some embodiments) query the user to confirm that such physical activity has occurred. If the user responds and confirms that the physical exercise has occurred, the continuous glucose monitoring system 600 may alert the user to cease the physical activity if the glucose levels are outside of a safe range or may prompt the user the manually adjust the user's insulin dosage. In other embodiments, the activity sensor 640 can include sensors, other than motion sensors, that can detect an increased activity level by detection one or more physiological parameters (e.g., the activity sensor can include a pulse rate sensor and not a motion sensor).

A number of embodiments have been described. Nevertheless, it will be understood that various modifications may be made without departing from the spirit and scope of this disclosure. For example, although the controller 200 and pump device 100 are described as separate removably attachable parts, in some embodiments, the infusion pump system can include a monolithic device including a pump device, with a drive system, and a controller. Accordingly, other embodiments are within the scope of the following claims.

What is claimed is:

1. An infusion pump system, comprising:
   a pump device including a drive system configured to dispense a medicine to a user;
   a first sensor configured to detect motion of the user indicative of a physical activity;
   a second sensor configured to detect information indicative of one or more numerical values of a physical characteristic of the user, wherein the second sensor is different than the first sensor; and
   a controller configured to activate the drive system to dispense the medicine to the user, the controller further configured to: (i) detect that the user has engaged in the physical activity based on information received from the first sensor; (ii) corroborate that the user has engaged in the physical activity based on information received from the second sensor and; (iii) adjust delivery of the medicine from the pump device to the user in response to detecting and corroborating that the user has engaged in the physical activity.

2. The infusion pump system of claim 1, wherein the first sensor comprises a motion sensor, the second sensor comprises a heart rate sensor, and the physical characteristic of the user comprises a heart rate of the user.

3. The infusion pump system of claim 2, wherein adjusting delivery of the medicine from the pump device to the user comprises reducing a rate of medicine delivery in response to identifying an increase in heart rate of the user based on information received from the heart rate sensor.

4. The infusion pump system of claim 1, wherein the second sensor comprises a blood pressure sensor, and the physical characteristic of the user comprises a blood pressure of the user.

5. The infusion pump system of claim 4, wherein adjusting delivery of the medicine from the pump device to the user comprises reducing a rate of medicine delivery in response to identifying an increase in blood pressure of the user based on information received from the blood pressure sensor.

6. The infusion pump system of claim 1, wherein the second sensor comprises a body temperature sensor, and the physical characteristic of the user comprises a body temperature of the user.

7. The infusion pump system of claim 6, wherein adjusting delivery of the medicine from the pump device to the user comprises reducing a rate of medicine delivery in response to identifying an increase in body temperature of the user based on information received from the body temperature sensor.

8. The infusion pump system of claim 1, wherein the second sensor comprises a perspiration sensor, and the physical characteristic of the user comprises a perspiration level of the user.

9. The infusion pump system of claim 8, wherein adjusting delivery of the medicine from the pump device to the user comprises reducing a rate of medicine delivery in response to identifying an increase in perspiration of the user based on information received from the perspiration sensor.

10. The infusion pump system of claim 1, wherein the second sensor comprises a respiration sensor, and the physical characteristic of the user comprises a respiration rate of the user.

11. The infusion pump system of claim 10, wherein adjusting delivery of the medicine from the pump device to the user comprises reducing a rate of medicine delivery in response to identifying an increase in respiration rate of the user based on information received from the respiration sensor.

12. The infusion pump system of claim 1, wherein the first sensor comprises a motion sensor, the second sensor comprises a muscle activity sensor, and the physical characteristic of the user comprises muscle activity of the user.

13. The infusion pump system of claim 12, wherein adjusting delivery of the medicine from the pump device to the user comprises reducing a rate of medicine delivery in response to identifying an increase in muscle activity of the user based on information received from the muscle activity sensor.

14. The infusion pump system of claim 1, wherein the second sensor comprises an inclination sensor.

15. The infusion pump system of claim 1, wherein the first sensor comprises a motion sensor and the second sensor comprises a physiological sensor.

16. The infusion pump system of claim 1, wherein determining that the user has engaged in the physical activity based on information received from the first sensor and the second sensor comprises detecting that the user has engaged in the physical activity based on information received from the first sensor and confirming that the user has engaged in the physical activity based on information received from the second sensor.

17. The infusion pump system of claim 1, wherein:
the first sensor comprises a motion sensor; and
determining that the user has engaged in the physical activity based on information received from the first sensor and the second sensor comprises detecting that the user has engaged in the physical activity based on motion detected by the first sensor and confirming that the user has engaged in the physical activity based detecting an increase in the one or more numerical values of the physical characteristic of the user using information received from the second sensor.

18. A method of administering medicinal fluid to a user, comprising:
delivering a medicinal fluid from a wearable pump system to the user;
detecting an activity level of the user using an activity sensor;
measuring a physical characteristic of the user using a physiological sensor;
analyzing information received from the physiological sensor to determine whether the detected activity level of the user as detected by the activity sensor represents an actual activity level of the user; and
adjusting the delivery of medicinal fluid from the pump system to the user in response to determining that the detected activity level represents the actual activity level of the user.

19. The method of claim 18, wherein detecting the activity level of the user using the activity sensor in the pump system includes detecting whether the user entered data into the pump system and determining if a detected motion of the pump system is within a threshold range of time from when the user entered data into the pump system, wherein the motion of the pump system is ignored if the motion of the pump system is within the threshold range of time from when the user entered data into the pump system.

20. The method of claim 18, further comprising determining whether a physical activity indicated by the detected activity level of the user could be dangerous and providing a notification to the user that the physical activity could be dangerous.

21. The method of claim 18, wherein:
the physiological sensor comprises a heart rate sensor;
the physical characteristic of the user comprises a heart rate of the user; and
analyzing information received from the physiological sensor to determine whether the detected activity level of the user as detected by the activity sensor represents an actual activity level of the user includes determining that the heart rate of the user has increased beyond a threshold amount.

22. The method of claim 18, wherein:
the physiological sensor comprises a respiration sensor;
the physical characteristic of the user comprises a respiration rate of the user; and
analyzing information received from the physiological sensor to determine whether the detected activity level of the user as detected by the activity sensor represents an actual activity level of the user includes determining that the respiration rate of the user has increased beyond a threshold amount.

* * * * *